(12) United States Patent
Matsuura et al.

(10) Patent No.: US 10,561,881 B2
(45) Date of Patent: Feb. 18, 2020

(54) DYNAMIC PROPRIOCEPTION

(71) Applicant: Tau Orthopedics, LLC, Rancho Santa Fe, CA (US)

(72) Inventors: Belinko K. Matsuura, Solano Beach, CA (US); David G. Matsuura, Solano Beach, CA (US); Kaitlin von Hoffmann, Coto de Caza, CA (US); Gerard von Hoffmann, Coto de Caza, CA (US)

(73) Assignee: TAU Orthopedics, Inc., Rancho Santa Fe, CA (US)

( * ) Notice: Subject to any disclaimer, the term of this patent is extended or adjusted under 35 U.S.C. 154(b) by 106 days.

(21) Appl. No.: 15/560,150

(22) PCT Filed: Mar. 23, 2016

(86) PCT No.: PCT/US2016/023715
§ 371 (c)(1),
(2) Date: Sep. 20, 2017

(87) PCT Pub. No.: WO2016/154271
PCT Pub. Date: Sep. 29, 2016

(65) Prior Publication Data
US 2018/0093121 A1    Apr. 5, 2018

Related U.S. Application Data

(60) Provisional application No. 62/137,036, filed on Mar. 23, 2015.

(51) Int. Cl.
*A63B 21/005* (2006.01)
*A41D 1/00* (2018.01)
(Continued)

(52) U.S. Cl.
CPC ............ *A63B 21/005* (2013.01); *A41D 1/002* (2013.01); *A41D 13/0015* (2013.01); *A63B 21/00185* (2013.01)

(58) Field of Classification Search
CPC ............ A63B 21/005; A63B 21/00845; A63B 21/4011; A63B 21/4017; A63B 21/4025;
(Continued)

(56) References Cited

U.S. PATENT DOCUMENTS 2,664,566 A    1/1954  Mianulli
2,832,334 A    4/1958  Whitelaw
(Continued)

FOREIGN PATENT DOCUMENTS

WO    2014138504    9/2014
WO    2014153201    9/2014
WO    2014194257    12/2014

OTHER PUBLICATIONS

Written Opinion Issued on PCT Application Serial No. PCT/US16/23715 by ISA/US dated Aug. 11, 2016, pp. 1-6.
(Continued)

*Primary Examiner* — Sisay Yacob
(74) *Attorney, Agent, or Firm* — Aurora Consulting LLC; Ashley Sloat

(57) ABSTRACT

A wearable device such as a garment is disclosed, having at least one resistance element at a motion segment such as a hip or knee. The garment includes at least one sensor, for sensing a parameter. Electronics are provided for processing the sensed parameter, and for providing feedback. Feedback may be in the form of proprioceptive tactile or audible feedback, or in the form of an adjustment of a performance parameter of the wearable device. In one implementation, resistance to movement of the wearer is adjusted up or down in response to changes in power output by the wearer.

32 Claims, 9 Drawing Sheets

(51) Int. Cl.
*A41D 13/00* (2006.01)
*A63B 21/00* (2006.01)

(58) Field of Classification Search
CPC .......... A63B 21/00185; A63B 23/0482; A63B
23/0494; A63B 24/0087; A63B
2024/0093; A63B 2071/0625; A63B
2071/065; A63B 2071/0655; A63B
2071/0666; A63B 21/00189; A63B
21/0053; A63B 21/008; A63B 21/0083;
A63B 21/0087; A63B 21/012; A63B
21/023; A63B 21/028; A63B 21/0552;
A63B 21/159; A63B 21/4039; A63B
21/4047; A63B 2209/08; A63B 2209/10;
A63B 2213/004; A63B 2220/12; A63B
2220/44; A63B 2220/51; A63B 2220/803;
A63B 2225/20; A63B 2225/50; A63B
2230/202; A63B 2230/205; A63B
2230/207; A63B 2230/42; A63B 2230/50;
A63B 2230/60; A63B 2230/65; A63B
2230/75; A63B 23/02; A63B 23/1245;
A63B 23/1281; A63B 71/0622; A41D
1/002; A41D 13/0015; A61B 5/0492;
A61B 5/6802; A61B 5/6804; A61B
2503/10; A61B 2562/0209; A61B
2562/0219; A61B 2562/04; A61B
2562/125; A61B 2562/164; A61B 5/002;
A61B 5/0205; A61B 5/1118; A61B 5/112;
A61N 1/0452; A61N 1/0484; A61N
1/36003; G06Q 10/0639; G06Q 50/22;
G09B 19/0038; G09B 23/28; H04M
1/7253
See application file for complete search history.

(56) References Cited

U.S. PATENT DOCUMENTS

| | | |
|---|---|---|
| 4,065,814 A | 1/1978 | Fox |
| 4,485,808 A | 12/1984 | Hepburn |
| 4,621,620 A | 11/1986 | Anderson |
| 4,657,000 A | 4/1987 | Hepburn |
| 4,829,989 A | 5/1989 | Deamer |
| 4,875,677 A | 10/1989 | Tetreault |
| 4,910,802 A | 3/1990 | Malloy |
| 4,947,835 A | 8/1990 | Hepburn et al. |
| 5,052,379 A | 10/1991 | Airy et al. |
| 5,176,600 A | 1/1993 | Wilkinson |
| 5,201,074 A | 4/1993 | Dicker |
| 5,263,923 A | 11/1993 | Fujimoto |
| 5,306,222 A | 4/1994 | Wilkinson |
| 5,308,305 A | 5/1994 | Romney |
| 5,337,737 A | 8/1994 | Rubin et al. |
| 5,399,154 A | 3/1995 | Kipnis et al. |
| 5,465,428 A | 11/1995 | Earl |
| 5,472,412 A | 12/1995 | Knoth |
| 5,527,244 A | 6/1996 | Waller et al. |
| 5,553,322 A | 9/1996 | Cebo-Johnson |
| 5,662,595 A | 9/1997 | Chesher et al. |
| 5,685,811 A | 11/1997 | McShane et al. |
| 5,720,042 A | 2/1998 | Wilkinson |
| 5,749,840 A | 5/1998 | Mitchell et al. |
| 5,788,618 A | 8/1998 | Joutras |
| 5,792,034 A | 8/1998 | Kozlovsky |
| RE35,940 E | 10/1998 | Heinz et al. |
| 5,842,959 A | 12/1998 | Wilkinson |
| 5,867,827 A | 2/1999 | Wilkinson |
| 5,875,491 A | 3/1999 | Wilkinson |
| 5,937,441 A | 8/1999 | Raines |
| 5,960,474 A | 10/1999 | Dicker et al. |
| 5,976,063 A | 11/1999 | Joutras et al. |
| 5,978,966 A | 11/1999 | Dicker et al. |
| 5,993,362 A | 11/1999 | Ghobadi |
| 6,039,677 A | 3/2000 | Spletzer |
| 6,129,638 A | 10/2000 | Davis |
| 6,176,816 B1 | 1/2001 | Dicker et al. |
| 6,186,970 B1 | 2/2001 | Fujii et al. |
| 6,210,354 B1 | 4/2001 | Ousdal |
| 6,231,488 B1 | 5/2001 | Dicker et al. |
| 6,314,580 B1 | 11/2001 | Greenberg et al. |
| 6,397,496 B1 | 6/2002 | Seymour |
| 6,409,693 B1 | 6/2002 | Brannigan |
| 6,440,094 B1 | 8/2002 | Maas |
| 6,656,097 B2 | 12/2003 | Karecki |
| 6,666,801 B1 | 12/2003 | Michalow |
| 6,757,916 B2 | 7/2004 | Mah et al. |
| 6,834,752 B2 | 12/2004 | Irby et al. |
| 6,872,187 B1 | 3/2005 | Stark et al. |
| 6,954,968 B1 | 10/2005 | Sitbon |
| 7,048,098 B1 | 5/2006 | Moradian |
| 7,087,003 B1 | 8/2006 | Katterjohn |
| 7,153,246 B2 | 12/2006 | Koscielny et al. |
| 7,235,038 B2 | 6/2007 | Liao |
| 7,599,806 B2 | 10/2009 | Hauschildt |
| 7,608,026 B1 | 10/2009 | Nicassio |
| 7,652,386 B2 | 1/2010 | Donelan et al. |
| 7,659,636 B2 | 2/2010 | Donelan et al. |
| 7,682,322 B2 | 3/2010 | Engelman |
| 7,744,511 B2 | 6/2010 | Grigoriev et al. |
| 7,758,481 B2 | 7/2010 | Drennan et al. |
| 7,845,023 B2 | 12/2010 | Surve et al. |
| 7,849,518 B2 | 12/2010 | Moore et al. |
| 7,861,319 B2 | 1/2011 | Torry |
| 7,874,970 B2 | 1/2011 | Glisan |
| 7,931,571 B2 | 4/2011 | Bernardoni |
| 7,931,609 B2 | 4/2011 | Blanchard |
| 8,043,243 B2 | 10/2011 | Nathanson et al. |
| 8,060,945 B2 | 11/2011 | Adarraga |
| 8,063,644 B2 | 11/2011 | Rezvani et al. |
| 8,171,570 B2 | 5/2012 | Adarraga |
| 8,273,001 B2 | 9/2012 | Karecki et al. |
| 8,312,646 B2 | 11/2012 | Meschter et al. |
| 8,409,117 B2 | 4/2013 | Cheng et al. |
| 8,544,114 B2 | 10/2013 | Williams et al. |
| 8,555,415 B2 | 10/2013 | Bradstreet et al. |
| 8,663,133 B2 | 3/2014 | Johnson et al. |
| 8,663,142 B1 | 3/2014 | Pansiera |
| 8,762,077 B2 | 6/2014 | Redmond et al. |
| 8,784,350 B2 | 7/2014 | Cohen |
| 8,870,798 B2 | 10/2014 | Coleman |
| 8,905,855 B2 | 12/2014 | Fitzpatrick et al. |
| 8,939,924 B1 | 1/2015 | Paulos |
| 8,951,136 B1 | 2/2015 | Booher |
| 8,986,177 B2 | 3/2015 | von Hoffman et al. |
| 9,192,806 B2 | 11/2015 | Mial |
| 9,204,811 B2 | 12/2015 | Wright |
| 9,327,156 B2 | 5/2016 | von Hoffmann et al. |
| 9,375,603 B2 | 6/2016 | Matsuura et al. |
| 10,304,230 B2 | 5/2019 | Chamdani et al. |
| 2004/0040064 A1 | 3/2004 | Mah et al. |
| 2004/0116260 A1 | 6/2004 | Drennan et al. |
| 2005/0101887 A1 | 5/2005 | Stark et al. |
| 2005/0148915 A1 | 7/2005 | Nathanson et al. |
| 2005/0239602 A1 | 10/2005 | Cordova et al. |
| 2005/0255975 A1 | 11/2005 | Horn |
| 2005/0261113 A1 | 11/2005 | Wilkinson |
| 2005/0275416 A1 | 12/2005 | Hervieux et al. |
| 2006/0000478 A1 | 1/2006 | Taylor et al. |
| 2006/0016649 A1 | 1/2006 | Gordaninejad et al. |
| 2006/0046910 A1 | 3/2006 | Rastegar et al. |
| 2006/0046913 A1 | 3/2006 | Squittieri |
| 2006/0079825 A1 | 4/2006 | Hilton et al. |
| 2006/0096818 A1 | 5/2006 | Moradian |
| 2006/0272071 A1 | 12/2006 | Mickle et al. |
| 2006/0287621 A1 | 12/2006 | Atkinson et al. |
| 2007/0010772 A1 | 1/2007 | Ryan |
| 2007/0016120 A1 | 1/2007 | Latronica et al. |
| 2007/0032359 A1 | 2/2007 | Toronto |
| 2007/0100265 A1 | 5/2007 | Gamada |
| 2007/0123997 A1 | 5/2007 | Herr et al. |
| 2007/0135279 A1 | 6/2007 | Purdy et al. |

(56) References Cited

U.S. PATENT DOCUMENTS

| | | |
|---|---|---|
| 2007/0219074 A1 | 9/2007 | Pride |
| 2007/0245835 A1 | 10/2007 | Hauschildt |
| 2008/0009771 A1 | 1/2008 | Perry et al. |
| 2008/0026917 A1 | 1/2008 | Campana |
| 2008/0108918 A1 | 5/2008 | Joutras et al. |
| 2008/0218310 A1 | 9/2008 | Alten et al. |
| 2008/0222769 A1 | 9/2008 | Natonson |
| 2009/0253325 A1 | 10/2009 | Brookstein et al. |
| 2009/0281394 A1 | 11/2009 | Russell et al. |
| 2010/0029224 A1 | 2/2010 | Urushihara et al. |
| 2010/0041527 A1 | 2/2010 | Miller |
| 2010/0075557 A1 | 3/2010 | Shteiyer |
| 2010/0077527 A1 | 4/2010 | Lee et al. |
| 2010/0144490 A1 | 6/2010 | Purdy et al. |
| 2010/0193304 A1 | 8/2010 | Böse et al. |
| 2010/0223717 A1 | 9/2010 | Foy et al. |
| 2010/0248915 A1 | 9/2010 | Gibson-Horn |
| 2010/0267525 A1 | 10/2010 | Tanner |
| 2010/0323859 A1 | 12/2010 | von Hoffmann |
| 2011/0010001 A1 | 1/2011 | Chung et al. |
| 2011/0111932 A1 | 5/2011 | Von Hoffmann et al. |
| 2011/0126335 A1 | 6/2011 | Schultz |
| 2011/0224585 A1 | 9/2011 | Hall |
| 2011/0231986 A1 | 9/2011 | Waldie et al. |
| 2011/0247127 A1 | 10/2011 | Pou |
| 2011/0266323 A1 | 11/2011 | Kazerooni et al. |
| 2012/0094811 A1 | 4/2012 | Karecki |
| 2012/0116258 A1 | 5/2012 | Lee |
| 2012/0122574 A1 | 5/2012 | Fitzpatrick et al. |
| 2012/0136231 A1 | 5/2012 | Markel |
| 2012/0225755 A1 | 9/2012 | Lloyd |
| 2012/0259255 A1 | 10/2012 | Tomlinson et al. |
| 2013/0040783 A1 | 2/2013 | Duda et al. |
| 2013/0085040 A1 | 4/2013 | Bowers |
| 2013/0130874 A1 | 5/2013 | Richardson et al. |
| 2013/0150218 A1 | 6/2013 | Mial |
| 2013/0190147 A1 | 7/2013 | Luo et al. |
| 2013/0207889 A1 | 8/2013 | Chang et al. |
| 2013/0247330 A1 | 9/2013 | Daul et al. |
| 2013/0260968 A1 | 10/2013 | Shkolnik |
| 2013/0298301 A1 | 11/2013 | Petrakis et al. |
| 2013/0338472 A1 | 12/2013 | Barber et al. |
| 2014/0109282 A1 | 4/2014 | White et al. |
| 2014/0135593 A1 | 5/2014 | Jayalth et al. |
| 2014/0173934 A1 | 6/2014 | Bell |
| 2014/0200121 A1 | 7/2014 | von Hoffmann et al. |
| 2014/0207030 A1 | 7/2014 | Hall |
| 2014/0222943 A1 | 8/2014 | Oleson et al. |
| 2014/0238153 A1 | 8/2014 | Wood et al. |
| 2014/0265677 A1 | 9/2014 | Orand |
| 2014/0278125 A1 | 9/2014 | Balakrishnan et al. |
| 2014/0278229 A1 | 9/2014 | Hong et al. |
| 2014/0296761 A1 | 10/2014 | Yamamoto et al. |
| 2014/0313049 A1 | 10/2014 | Doherty |
| 2014/0336020 A1 | 11/2014 | von Hoffman et al. |
| 2014/0358053 A1 | 12/2014 | Triolo et al. |
| 2014/0364771 A1 | 12/2014 | Pitts et al. |
| 2014/0379275 A1 | 12/2014 | Yuen et al. |
| 2015/0031970 A1 | 1/2015 | Lain |
| 2015/0045703 A1 | 2/2015 | Strausser et al. |
| 2015/0057128 A1 | 2/2015 | Ishii |
| 2015/0148619 A1 | 5/2015 | Berg et al. |
| 2015/0149104 A1 | 5/2015 | Baker et al. |
| 2015/0190669 A1 | 7/2015 | Matsuura et al. |
| 2015/0230719 A1 | 8/2015 | Berg et al. |
| 2015/0258360 A1 | 9/2015 | von Hoffman et al. |
| 2016/0007885 A1* | 1/2016 | Basta ............... G16H 20/30 482/5 |
| 2016/0008206 A1* | 1/2016 | Devanaboyina ....... A47C 9/002 601/136 |
| 2016/0038783 A1 | 2/2016 | Matsuura et al. |
| 2016/0062333 A1 | 3/2016 | Jayaraman |
| 2016/0107309 A1 | 4/2016 | Walsh et al. |
| 2016/0128632 A1 | 5/2016 | Wiebe et al. |
| 2017/0090554 A1 | 3/2017 | Pececnik |

OTHER PUBLICATIONS

International Search Report Issued on PCT Application Serial No. PCT/US16/23715 by ISA/US dated Aug. 11, 2016, pp. 1-4.

* cited by examiner

DYNAMIC PROPRIOCEPTION

CROSS REFERENCE TO RELATED APPLICATIONS

This application is the U.S. National Stage Application under 35 U.S.C. 371 for PCT Application Serial No. PCT/US2016/023715, filed Mar. 23,2016,which claims the priority benefit under 35 U.S.C. § 119 (e)of U.S. Provisional Patent Application No. 62/137,036, filed

BACKGROUND OF THE INVENTION

A wide variety of portable or wearable devices are known, for tracking steps, GPS location, heart rate, and variety of additional biometric parameters. However, a need remains for devices which produce a responsive change in the behavior of the wearer and, preferably, in a performance characteristic of the wearable device.

SUMMARY OF THE INVENTION

There is provided a dynamic proprioception garment, comprising a waist region, a right leg and a left leg; a resistance unit associated with at least one of the right and left leg; a sensor; and an effector for providing proprioceptive feedback to a wearer of the garment. At least one effector may be carried on the left leg and at least one effector on the right leg. At least one effector may be carried on the posterior of the left leg and at least one effector on the posterior of the right leg.

The dynamic proprioception garment may comprise electronics configured to receive data from the sensor, process the data and activate at least one effector in response to a characteristic of stride reaching a preset value. The resistance unit may comprise a housing and the electronics may be carried within or coupled to the housing. The characteristic may comprise stride rate or stride length.

The location of the effector maybe correlated with a parameter of interest. The location of the effector may be correlated with information relating to at least one of blood oxygen saturation, heart rate, body temperature, power exertion, or respiration rate.

The effector may be configured to elevate or decrease the resistance provided by the resistance unit, in response to data obtained by the sensor, such as delivered power, exertion, or heart rate.

There is also provided a method of providing dynamic proprioception feedback to a wearer of a garment. The method comprises sensing a parameter measured on the wearer; processing the parameter to compare to a preset reporting alarm limit; and activating an effector to alert the wearer that the parameter has reached the alarm limit. The activating an effector step may comprise activating an effector associated with a location on the wearer to convey information to the wearer that is conveyed by the combination of the activation of the effector as well as the location of the effector. The sensing step may be accomplished by a sensor carried by the garment. Throughout this specification a reference to something being carried by the garment includes things being carried directly by the garment or indirectly such as within or attached to a housing or other component carried by the garment. The sensing step may be accomplished by a sensor carried by a device remote from the garment.

The device may be a wrist worn device, and may be a device in wireless communication with the garment. The activating an effector step may comprise activating the effector at a first intensity when a first alarm limit is reached, and activating the effector at a second intensity when a second alarm limit is reached. The activating an effector step may comprise activating the effector for a first duration when a first alarm limit is reached, and activating the effector for a second duration when a second alarm limit is reached.

A garment is provided for determining a metric of incremental effort exerted in response to an increased load. The garment comprises at least one resistance unit for increasing the load on a wearer during movement; a sensor on the garment for detecting at least one parameter that is associated with exerted effort; a processor for determining the incremental effort exerted by the wearer as a result of the load created by the resistance unit.

The garment may further comprise an output for outputting a metric of the incremental load. The output may be displayed on a visual display. The output may be displayed in watts and or calories.

DETAILED DESCRIPTION OF THE PREFERRED EMBODIMENT

A form-fitting wearable construct such as an interactive garment in accordance with the present invention may include at least one sensor and associated processing and communications electronics, and at least one effector which provides feedback and/or adjustment to the garment in response to data collected by the sensor and interpreted by the processor.

Figure 1:
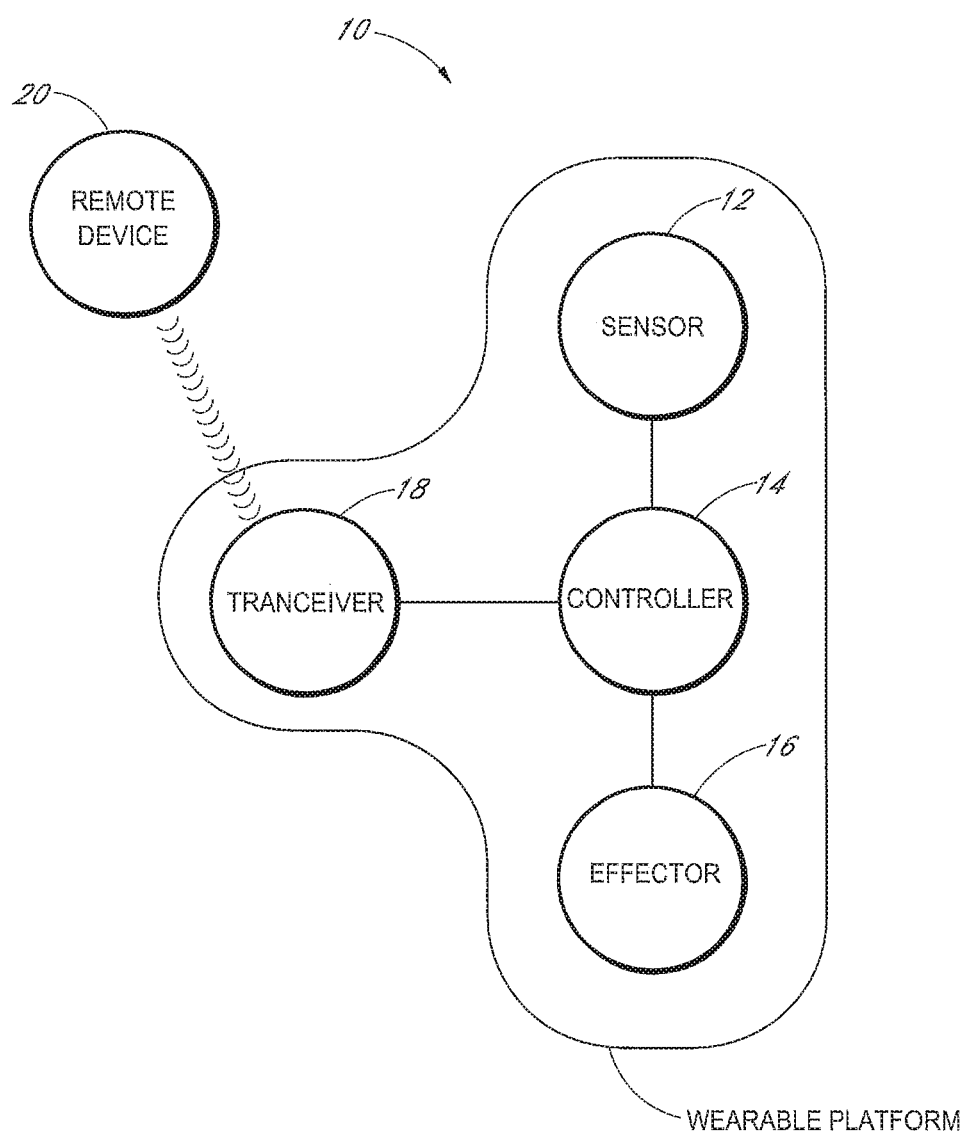
FIG. 1 is an overview of a dynamic proprioception system in accordance with the present invention.

Referring to FIG. 1, there is illustrated a schematic representation of a dynamic proprioception system in accordance with the present invention. The system 10 includes at least one sensor 12, described in greater detail below. The sensor 12 is in electrical communication with a controller 14. Controller 14 is in communication with at least one effector 16, for providing proprioceptive feedback and/or adjusting a physical parameter of the garment such as resistance to movement, compression or other parameter that will be perceptible to the wear. The controller 14 may additionally be in communication with a transceiver 18, for communication with a remote device 20. In certain embodiments, all of the foregoing components are carried by a wearable platform such as a garment 22. Specific examples of different types of sensors, controllers, effectors and transceivers will be discussed in greater detail below.

One or more sensors carried by the garment or the wearer of the garment can include, for example, electromyography (EMG), electrocardiograph (ECG), respiration, galvanic skin response (GSR), temperature, acceleration, bend angle, pressure, force, torque, GPS, accelerometer (single or multi axis), respiration, perspiration, bioimpedence, gyroscopes, various rate measurements such as stride rate, flex rate, pulse rate, spatial deviation or position, oxygen saturation, blood glucose, or others described elsewhere herein. The use of multiple sensors for the same parameter or multiple sensors for multiple parameters may provide a level of insight that is not available by measuring only a single metric such as heart rate (HR) or motion based on accelerometers or other types of motion sensors (e.g., a gyroscope).

These sensors may be incorporated in a permanent manner into the fabric of the form-fitting interactive garment itself or in a detachable manner such as with zippers, snap fit connectors, clasps, hook and loop (Velcro) or other releasable connectors and/or in pockets or under or on top of flaps if desired, to allow removal and/or repositioning of the sensors. Sensors may be carried by or within the resistance housing, especially sensors such as those relating to force, stride rate, and stride length.

A performance characteristic of the garment may be modified and/or tactile feedback provided to the wearer by selective activation of one or preferably a plurality of effectors in response to data collected by the sensor. For example, in a garment which provides resistance to movement across a joint such as the hip, knee or elbow, or a more complex motion segment such as the shoulder or abdomen, the resistance provided by a magnetorhelogical liquid damper as discussed elsewhere herein is adjusted up or down to achieve a desired result. Proprioceptic, visual, audio or other tactile feedback can be provided to the wearer to signal to the wearer that they should adjust their posture, or adjust a performance parameter such as increase or decrease stride length or repetition rate, realignment of stride, modify arm swing such as bring the elbows in or other streamlining adjustment, or adjust their spine (core) such as to bring it into alignment with a preset data set, or initiate other motion or body position correction.

Thus, any of a variety of effectors 16 may be provided in accordance with the present invention, to provide behavior modifying feedback or to modify garment performance. The effectors may provide visible, tactile, and/or audio feedback, depending upon the desired performance result. Effectors 16 thus may include structures such as vibrators, pressure generators such as inflatable balloons or electromechanical structures such as a solenoid involving motion or application of localized pressure to the wearer. Effectors may also apply an electrical current to the dermal surface, such as to produce an electrical shock or muscular stimulation. Effectors may produce sound, or provide a visual indicator such as a light or information on a local display such as a watch, cell phone, head worn display or other local display device.

Effectors may additionally include devices that produce a constriction or expansion of the garment along predetermined planes, in response to measured parameters. For example, at least a portion of a pant leg or other portion of the garment may be provided with an inflatable reservoir such as a balloon that can be inflated by a small pump, to increase compression against the wearer. Compression can alternatively be achieved using a device or material that can shorten in length upon activation such as NiTinol wires or fabric which shorten upon application of a current, or a motor driven take up spool. Such devices can be used to selectively constrict either around a circumference of a body part such as a waist, thigh, calf, arm, core (abdomen) etc., or along a preselected axis such as to apply compression or to change posture across a shoulder or body core.

Figure 2:
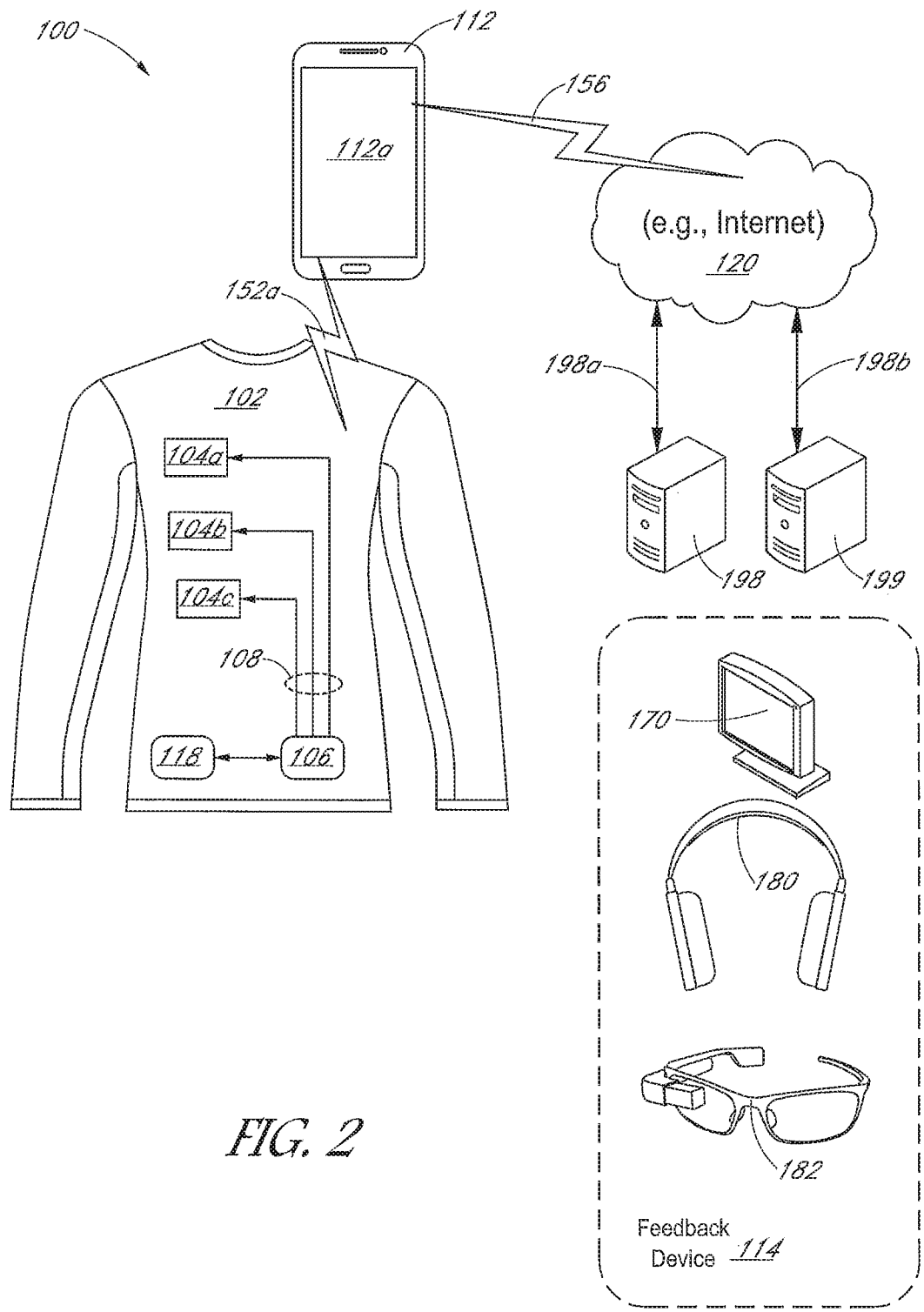
FIG. 2 is a further overview of the dynamic proprioception system.

With reference to FIG. 2, there is depicted a form-fitting sensor garment 102, representing a compressive, stretchable, and form-fitting garment to be worn by a human subject (not shown). Although garment 102 is shown to be a shirt, it can take any other garment form factor including but not limited to shorts, yoga pants, compression pants, elbow pad, knee pad, undergarment, neck wrap, glove, and the like, etc.

Details of some exemplary sensors are discussed below. The one or more sensors may be washable sensors that may be carried by a garment and configured to be unaffected and/or undamaged by washing or otherwise cleaning or maintaining the garment. One or more form-fitting sensor garments may be made to be conformal to any part of the human body as desired. Typically, shirts, pants, shorts, cuffs such as for surrounding an elbow, knee or abdomen will be used. Stretchable, compressive and form-fitting fabric made of natural or preferably synthetic fibers (e.g., nylon, lycra, polyester, spandex, or other suitable fibers and blends thereof) may be configured to exert a biasing force on the sensors, which may be built-in to the form-fitting sensor garment, to bias (e.g., increase contact force) the washable sensors against the skin to maintain good electrical and/or mechanical contact and to reduce motion artifacts that may be caused if there is relative motion between the skin and the sensor(s) (e.g., the sensors and/or skin sliding against each other along their mutual contacting surfaces).

One implementation of the invention involves providing tactile feedback and/or adjusting resistance to motion in response to a sensed parameter such as a metric of muscle force or strength across the relevant motion segment. Although not a direct measurement of strength, electromyography measurements appear correlated to muscle activity and strength, and can be noninvasively measured by a sensor in contact with the skin. Typically, a pair of electrodes and associated electronics may form a sensor, which may receive as inputs a potential difference generated on the human skin due to ions flowing in muscle fibers as a result of muscle activity. Other sensors such as proximity sensors or strain gauges can also be used, as is discussed elsewhere herein.

In the following discussion, electromyography sensors are described only as an example. It should be understood, however, that the present application contemplates that other types of sensor may be implemented additionally and/or alternatively to the electromyography sensors discussed in connection with the examples herein, including any one or a combination of the sensors mentioned previously herein. In one or more embodiments, multiple washable electromyography (WE) sensors may be used to measure muscle activity at different sites on the human body. The WE sensors may be configured to measure muscle activity associated with different muscles to measure muscle exertion intensity. When groups of muscles are measured together, more complex analysis and feedback may be performed and made available to the user (e.g., tactile, and/or wirelessly via an application (APP) running on a smartphone, tablet, pad, or the like). Additional details of suitable WE sensors are disclosed in US patent publication No. 2014/0135593 to Jayalth et al., the disclosure of which is hereby incorporated by reference in its entirety herein.

The set of WE sensors may be removably carried by or permanently incorporated into the fabric of the form-fitting sensor garment. In one or more embodiments, the form-fitting sensor garment may come in various sizes to accommodate various body sizes (e.g., similar to the sizing system currently used with exercise or casual clothing). In one or more embodiments, it is recognized that the difference in skin condition and/or subcutaneous fat content from human subject to human subject may give rise to data acquisition error if left uncorrected. For example, electrode acquired signals from a user with a higher body fat percentage may differ from electrode acquired signals acquired from a leaner user even though they both may weigh the same and may fit into the same size garment. The subcutaneous fat layer between muscle tissue and skin surface may attenuate an electromyography signal resulting in different acquired amplitudes for different body types. The electrode acquired signal may be calibrated, in one or more embodiments, to improve analysis and feedback accuracy.

The number of electrodes/sensors that are built into the fabric can exceed the number actually required to obtain the necessary muscle activity data. Logic and/or heuristics may be employed to select the sensors that provide the best signals for the group of muscles of interest. This is particularly advantageous since the human subject may position the garment slightly differently at different times or in different work-out sessions. Further, the optimal measurement sites for one user may be different from the optimal measurement sites for other users. Prior to physical activity such as work out, intelligent logics and/or algorithms may be employed to select the optimal group of sensors on the form-fitting sensor garment to use for actual monitoring and analysis. As another example, the user may be guided to engage in a training or a teaching routine to allow the textile-based monitoring, analysis and feedback systems (MAF's) to properly recognize and select the optimal group of sensors on the form-fitting sensor garment to use in the actual monitoring and analysis. Signals from sensors that are not selected may be ignored or given less weight or may be employed in other ways, for example.

All sensor data from all available sensors may be collected and/or stored (e.g., in memory), and analysis may be performed only on the subset of sensors that are relevant and/or deemed to generate most optimal signals for analysis. In other embodiments, only the relevant subset of sensor data may be collected and/or stored and/or analyzed. One or more of the collecting, the storing, or the analyzing may occur internally (e.g., on one or more processors or controllers in the garment), externally (e.g., in an external device such as the smart personal communications device (SPCD) or other wireless device) or both.

The design of the garment and geometry of the electrodes may be configured to account for variations in user body types and resulting alignment concerns. Intuitive features may be added to the garment to ensure proper alignment. These may include, but are not limited to, visible lines, markers and cut-outs for thumb, elbow, etc. For example, alignment marks or markers including but not limited to visible lines may provide a guide where the user only needs to ensure the line is straight for proper alignment. The electrode geometry may be designed to account for different muscle sizes.

In one example, increasing a dimension of the electrode orthogonal to the muscle fiber direction may accommodate varying fiber radii and resulting muscle volume. In other examples, the garment may include designed structures configured to urge and/or force the user to correctly position the garment and its sensors with proper orientation with respect to the muscles or other portions of the user's body to be sensed. For example, a shirt-like garment may include a cut-out portion for one or more body parts such as one for an elbow and another for a thumb and/or one or more fingers. The user aligning the elbow cut-out with the elbow of his/her arm and the fingers and/or thumb with their respective cut-outs may be used to ensure at least approximately accurate alignment of sensors in an arm portion of the shirt-like garment with the muscles in the arm that are to be sensed by the sensors disposed in the arm portion of the shirt-like garment.

As another example, a pant-like garment (e.g., Yoga pant or compression pant or short) may include for each leg, a heel loop and a knee cut-out configured to align sensors in a leg portion of the pant-like garment with the intended muscles in the user's legs. Other types of design structures may be configured into a garment where appropriate and may be used in conjunction with one or more alignment marks included with the garment. The above are non-limiting examples of designed structures and the present application is not limited to the above examples.

The wearer may be given real-time feedback based on analysis of the sensor outputs. For example, pattern recognition algorithms may be employed to detect whether the muscle exertion data from a group of muscles indicates that the user is engaging in incorrect form or in a non-optimal workout or other activity compared to reference data. For example, exercises targeting the biceps brachii are meant to isolate exertion of that muscle from the rest of the body. A less efficient workout occurs when the user generates momentum using the shoulder and/or lower back. Identifying activity in these momentum-influencing muscles can determine incorrect form. Accelerometer or bend-angle data may be incorporated to complement the aforementioned. The feedback may be made in visual or audible form to allow the user to easily understand muscle activity and how to improve and/or correct a workout routine. In this manner, virtual coaching may be accomplished in real time to coach the user over the course of the workout. Preferably for many applications the feedback includes tactile feedback, such as by activation of effectors such as small vibrators at selected positions on the garment or adjacent wearable support, as is discussed elsewhere herein. Electrical current (perceptible shock or muscle stimulation), heat, inflation of small balloons or other temperature or pressure generating tactile feedback assemblies may also be used.

The interactive garment may be part of a textile-based human MAF system. Processing and communication electronics on the form-fitting sensor garment may allow for data exchange (e.g., via a wireless communications link) with the exercise equipment, the SPCD (e.g. smart phone), the feedback device and/or the Internet (e.g., computers implemented remotely and available via the Internet).

In the following discussion, concepts of the present application will be described primarily using athletics as well as strength and conditioning as an example application. Other applications such as medical rehabilitation or realignment or training of balance or perceived spatial orientation or training a wearer to follow a predetermined routine such as a dance or athletic activity are also contemplated. The end use application in which the sensors and garment described herein may be used does not change the form or function of the concepts described in the present application. For example, applied to ergonomics the ability to critique form and posture and provide proprioceptive feedback as discussed herein can be used to train proper procedures in a manufacturing environment, work environment, and athletic endeavors, just to name a few. Critiquing posture may provide injury prevention in the workplace in the same way as in an athletic training setting. As another example, in that the present application builds on clinical methods and provides a more user-friendly experience, the present application may be applied for use in self-guided medical rehabilitation and injury prevention training.

Referring to FIG. 2, a plurality of sensors 104A, 104B, and 104C are schematically depicted as being disposed at various positions on the fabric of garment 102. The actual number and location of the sensors will depend upon the desired functionality of the system, as will be apparent to those of skill in the art.

Although only three sensors (104A-104C) are depicted, it should be understood that there is no limit to the number and different types of sensors that may be employed and more or fewer sensors may be implemented than are depicted in the example of FIG. 2. Sensors such as electro-myography, gyroscopes, magnetometers, accelerometers, temperature, GSR, HR, bioimpedance, etc., and others disclosed elsewhere herein may be used as or in combination with sensors 104A-104C.

The electrodes of sensors that benefit from direct dermal contact may be disposed on the inside of the garment such that they make direct contact with the skin generally at locations where muscles of interest are expected to be located adjacently when the garment 102 is worn. In another embodiment, the electrodes may be formed externally to the garment 102 so that they do not make direct contact with the skin but are electrically coupled to the bio potential signals from the skin proximate the electrodes position in the garment 102. Certain sensors (e.g., accelerometers, gyroscopes, etc.) do not depend upon and some may even desirably avoid dermal contact, and may be mounted in any convenient and appropriate manner to the garment.

Typically, electrodes of sensors 104A-104C may comprise a conductive material bonded or woven or a conductive resin (e.g., polymers, silicone, neoprene, thermoplastics, etc.) applied through a screening, printing or gluing process, or combination thereof, in either a permanent or detachable manner, to the fabric or to another conductive substrate attached to the fabric of the form-fitting sensor garment 102. The electrodes may be formed from a flexible PCB substrate (e.g., Kapton or other laminates) that may be bonded to the garment 102. Thus, the user does not have to manually attach the electrodes to different specific locations on the skin in the manner required for conventional physiological monitoring apparatus. In the example herein, sensors 104A-104C may be washable electromyography sensors although it should be understood, as mentioned, that other types of sensors may well be alternatively or additionally employed.

Preferably, sensors 104A-104C are constructed such that they may withstand repeated wash-and-dry cycles typical of wearable clothing. Form-fitting sensor garment 102 may be made from materials, circuitry, structures or the like that may be amendable to any number of wash cycles (e.g., in a washing machine or hand washing) and/or drying cycles (e.g., in a gas or electric dryer). Form-fitting sensor garment 102 may be made from materials, circuitry, structures or the like that may be amendable to dry-cleaning processes and the chemicals used in dry-cleaning processes. However, in some applications it may be preferable to hang-dry (e.g., air dry) garment 102, to preserve an appearance of the material (e.g., fabrics, colors, dyes, etc.) used for the garment 102, to prevent dryer lint or the like from gathering on the garment 102, and to prevent damage to the garment 102, its electronics, fabrics, sensors, or the like due to inadvertently drying the garment 102 at too high a temperature. In some applications garment 102 may be configured for machine drying, air drying, or both. Some sensors, effectors (e.g., vibrators) and performance adjustment mechanisms (e.g., dampers) may be removably mounted to the garment so they can be removed prior to washing the garment. Actual washing and/or drying instructions and/or processes for the garment 102 will be application dependent and are not limited to the examples described herein.

The sensors may be incorporated into an interactive garment in a permanent manner or a detachable manner. In some examples, the sensors are detachably mounted to the garment for a purpose including but not limited to washing the garment, re-positioning on the garment, repairs, replacement, upgrades, updates to software, sensor calibration, power source maintenance, to install on a different garment, to exchange for another sensor or type of sensor, just to name a few.

Figure 3:
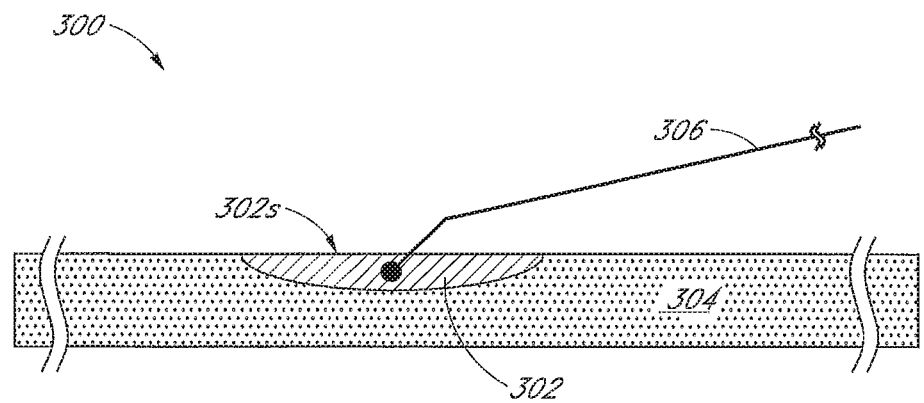
FIG. 3 is a cross-sectional view of a wearable sensor.

Attention is now directed to FIG. 3 where one example of an electromyography electrode 300 is depicted. In FIG. 3, an electrode base 302 may be formed using a conductive resin (e.g., silicone, neoprene, rubber, polymers, thermoplastics, etc.). The electrode base 302 may be formed directly, in some examples, on fabric 304 of the form-fitting sensor garment 102. Electrode base 302 may be deposited by a process similar to painting such as silk-screening, printing, or other processes for depositing or otherwise forming an electrically conductive material on another material, such as on fabric 304, for example. One or more portions of a surface 302s of electrode base 302 may be urged into contact with skin of a user who dons garment 102. Surface 302s may have any shape or surface profile (e.g., planar, arcuate, undulating, etc.) and is not limited to the configuration depicted in FIG. 3.

A conductive lead 306, which may be formed of a conductive material (e.g., an electrically conductive material) or a fiber optic material (e.g., a plastic or glass fiber optic cable or optical waveguide), is depicted as being embedded in electrode base 302 and may serve as the signal conduit between the sensor electronics and the electrode 302. Conductive lead 306 may likewise be deposited by a process similar to painting such as silk-screening or printing or may be conductive traces laminated in a flexible and/or stretchable PCB substrate, flexible printed circuitry (FPC), or flat flexible cable (FFC), that is then adhered onto the garment 102 (e.g., on an interior or exterior surface of the garment 102). In some applications, it may be desirable for esthetic, industrial design, fashion, practical, or trouble-shooting reasons to position some or all of the conductive lead(s) 306 on an exterior surface of the garment 102 so that they are visible to the human subject or others when the garment 102 is worn. Using the conductive lead(s) 306 for esthetic, industrial design, or fashion reasons may make the conductive lead(s) 306 hide in plain sight and not be recognized as conductive lead(s) 306 for a sensor enabled garment, but rather as design elements of an article of clothing or allow the garment 102 to be worn in scenarios (e.g., for casual dressing or as sporty clothing) other than those associated with sensing data from muscle activation as described herein.

In an embodiment, lead 306 may be permanently attached to electrode base 302. In another embodiment, lead 306 may be detachable, using a detachable connector configured to couple with a corresponding connector of electrode base 302. In either case, a pair of leads 306 coupled with two neighboring electrodes 302 may permit the sensor electronics to sense the potential difference between the electrodes 302 and outputs a difference between the potentials (or a processed version thereof) as an output signal(s).

Figure 4:
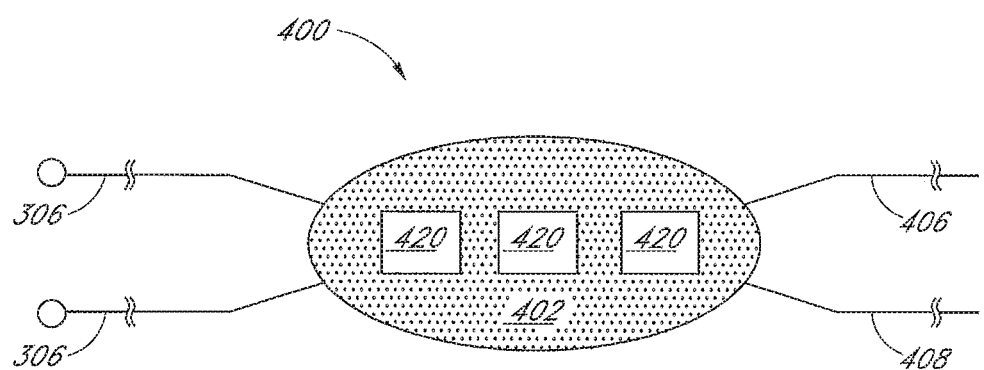
FIG. 4 is a top plan view of a wearable sensor.

FIG. 4 depicts one example 400 of an implementation of sensor electronics. In FIG. 4, sensor electronics 420 (such as integrated circuits (IC's), ASIC's, FPGA's, programmable logic, conductors, circuit boards, and/or discrete components) may be embedded in a sensor base 402 to secure the electronic components of sensor electronics 420 in place as well as to protect the electronic components that comprise the sensor electronics 420 from the outside environment (e.g., exposure to the elements and/or physical damage). Electronics may alternatively be located within or carried by the resistance unit, or electronics module connectable to the resistance unit. Sensor base 402 may preferably formed of a non-conductive resin (e.g., a non-conducive rubber-like potting material) and is preferably chosen for durability in the human exercise environment as well as in repeated wash-and-dry cycles. Conductive leads 306, which are in electrical communication with electrode bases 302 of FIG. 3, may be coupled with the sensor electronics 420 of sensor base 402 in a permanent or detachable manner.

In an embodiment, sensor base 402 may be formed directly on the fabric or other material of the form-fitting sensor garment 102. As before, the sensor base 402 may be deposited by a process similar to painting such as silk screening or printing as described above for lead 306. Sensor base 402, along with the sensor electronics 420, may be permanently attached to the fabric of the form-fitting sensor garment or may be made detachable. Velcro or other mechanical fasteners may be employed if a detachable implementation is desired. An output lead 406 may be coupled, in a permanent or detachable manner, with the sensor electronics 420 to output the sensor signal(s). In an embodiment, signal communication may be wireless in which case an output lead (e.g., 306, 406, 408) may not be necessary. One or more conductors 408 may also be coupled with the sensor electronics 420, in a permanent or detachable manner, to provide power (e.g., from battery pack 118), ground, other signals, etc. In some examples, power for sensor electronics 420 may be positioned in or on sensor base 402. In other examples, sensor base 402 may be configured to be detachable from garment 102. Detachment may allow for one or more of sensor re-positioning on the garment 102, charging, replacing, or servicing a power source (e.g., rechargeable battery) for the sensor electronics 420. In yet other examples, sensor base 302 and sensor electronics 402 may be detachably connected with each other.

Figure 5:
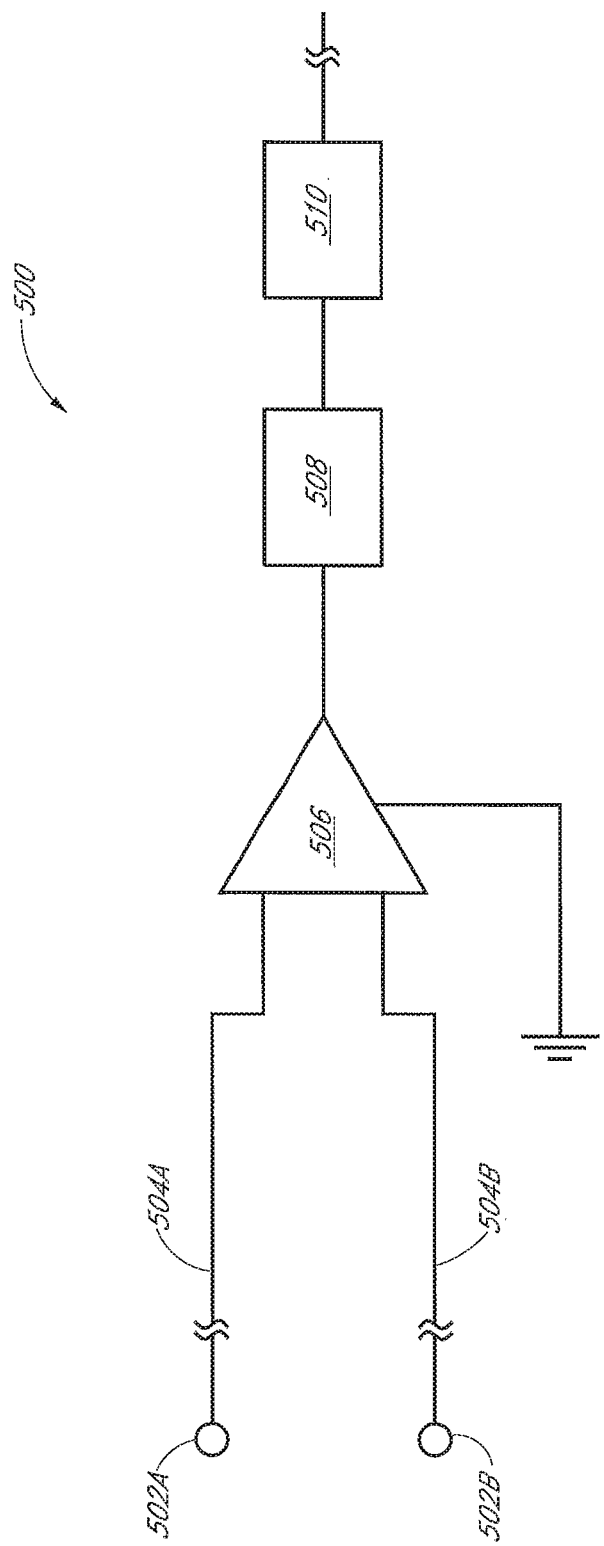
FIG. 5 is a simplified electronic sensor circuit.
Figure 6:
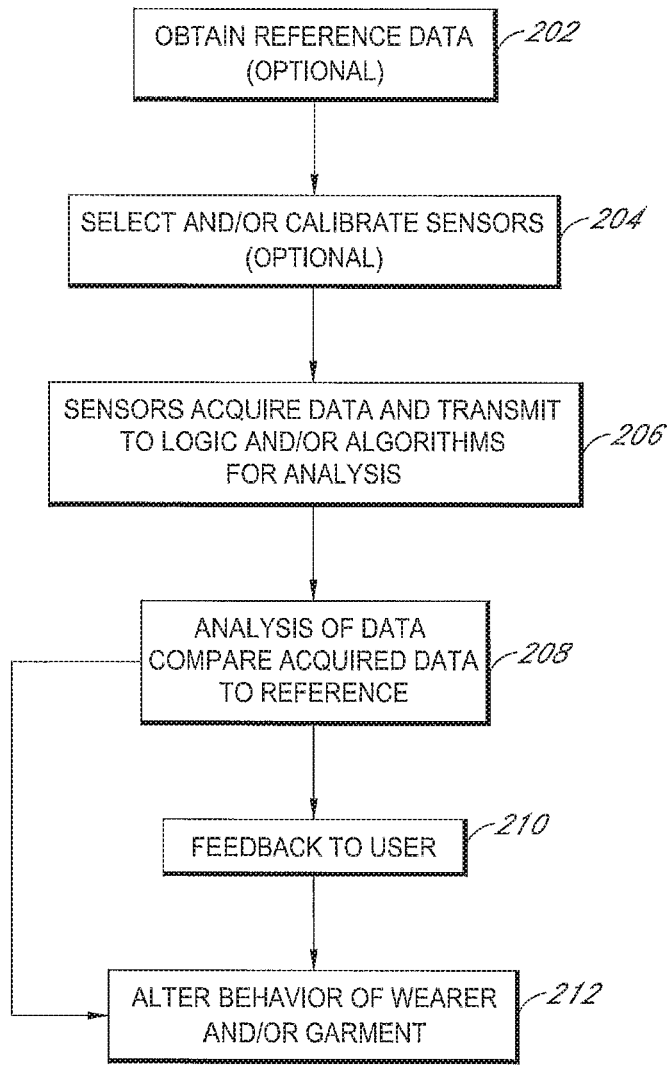
FIG. 6 is a flow diagram illustrating data capture, data processing, and feedback to the user or adjustment of a characteristic of a wearable device.

FIG. 5 depicts one example 500 of electronic circuitry that may be included in sensor electronics 420. The acquired signals from electrodes 502A and 502B (e.g., from leads 306) may be received by differential amplifier 506 via leads 504A and 504B respectively. Amplifier 506 may act as a voltage amplifier to amplify, in some examples, a difference between sensed signals. An output of amplifier 506 may be further processed via filter block 508 to amplify and isolate a frequency spectrum of a physiological signal.

Any of a variety of stretch or strain gauge sensors may be used. Suitable elastic strain sensors are disclosed, for example, in US patent publication No. 2014/0238153 to Wood, et al., the disclosure of which is incorporated in its entirety herein by reference.

Any of a variety of piezoelectric sensors may be utilized to sense, for example, stretch at the skin surface or pressure such as between the anterior of a lower leg and a posteriorly directed force from a garment having a resistance element. Piezoelectric sensors have a proven history of versatility and reliability in measuring pressures and forces. Suitable sensors include Model #A401 FlexiForce Standard and Force Load commercially available from Tekscan, Inc. (South Boston, Mass.). See US patent publication No. 2014/0364771 to Pitts, et al., the disclosure of which is incorporated in its entirety herein by reference. This sensor model has a thickness of about 0.208 mm, a length of about 56.8 mm, and a width of about 31.8 mm. The approximate sensing area is 25.4 mm in diameter and the substrate material is composed of polyester so the sensor can take the form of a flexible strip or patch which can conform to the shape of the adjacent dermal surface.

Various other force sensors may also be utilized. Sensors used should be resilient to twisting, tension, and wet conditions to ensure the device will continue to perform as intended and to determine the expected life of the product.

At least one or two or four or more accelerometers may be placed throughout the garment (e.g., left and right arm; left and right leg) and/or otherwise carried by the wearer's body (i.e., attached via any suitable manner to shoes, wrist bands, etc.) to collect multiple data points. Each of the additional accelerometers may be connected wirelessly or via electrical conductors back to the controller 14 or transceiver 18. A processor in the controller 14 may be preprogrammed to analyze and export the data in terms of g-force, impact, impact force, total acceleration, initial acceleration. The user may also choose to represent performance data (e.g., height, ascent or descent angle, ascent or descent velocity, ascent or descent force, force in terms of strength required to stay in position, relative position, etc.) to visual data (e.g., spreadsheet, statistical report, graph, etc.) or video overlay graphic for post event downloading onto a computer for viewing. The wearer can preset alarm limits so that tactile feedback is provided in real time upon the occurrence of a predetermined event (e.g., if a maximum or minimum limit is exceeded on any of the measured parameters)

A suitable 3-axis accelerometer may be a model ADXL377 available from Analog Devices, Inc. of Norwood, Mass. or any equivalent. Likewise, a suitable 3-axis gyroscope may be a model ADXRS652 available from Analog Devices, Inc. of Norwood, Mass. or any equivalent. Raw data may be sent from both the 3-axis accelerometer and the 3-axis gyroscope to the controller 14 which can record acceleration and 3-axis gyroscope position in terms of x, y, and z coordinates. The controller may obtain position point recordings 500 times a second and is configured to automatically write the data points to memory along with transmitting the data over the communication interface to sensor data interpretation software which may be resident on a remote computing device (e.g., laptop, cell phone, etc.). Additional details of wearable gyroscope and accelerometer systems may be found in US patent publication 2014/03133049 to Doherty, the entirety of which is hereby incorporated by reference herein.

Referring back to FIG. 2, a controller 106 may be coupled with sensors 104A-104C via a network of flexible signal conductors 108 (which may be electrically conductive or optical). In one embodiment, sensors 104A-104C may communicate with controller 106 via a wired (e.g., hard wired) interface. In another embodiment, sensors 104A-104C may communicate with controller 106 via a wireless interface that may use a variety of wireless protocols described elsewhere herein. Preferably, signal conductors 108 may be constructed such that they can also withstand repeated wash-and-dry cycles or wash and hang-dry cycles that typical of wearable clothing. Bonded insulated conductors, such as Kapton and laminate based printed circuit boards, wire, cable, coaxial conductors, shielded conductors, flexible printed circuits (FPC), flat flexible cable (FFC), electrically conductive threads, or silk-screened/printed electrically conductive resins are examples of technologies that may be used to implement signal conductors 108. In some examples, sensors 104A-104C may communicate with controller 106 using a combination of wired and wireless communications links. Controller 106 may comprise one or more controllers or one or more processors. In some examples controller 106 may alternatively be referred to as a processor or processor 106.

Typically, controller 106 may include communication electronics (e.g., one or more radios for a wireless communications link) to permit form-fitting sensor garment 102 to communicate (e.g., wireless data) with one or more of external, remote devices such as a smart personal communication device (SPCD) 112 (e.g., a smart phone, tablet, or pad), remote feedback device 114, on board feedback device 110 such as a vibrator, compression pad or ring, electrical current or other effector as discussed elsewhere herein, or the Internet 120 via an appropriate router/access point arrangement, such as a wireless network (e.g., Bluetooth (BT), BT Low Energy, NFC, WiFi, any variety of IEEE 802.x, etc.). The electronics for implementing controller 106 may be permanently attached to the fabric of form-fitting garment (in which case controller 106 may be constructed such that it can withstand repeated wash-and-dry and/or wash and hang dry cycles typical of wearable clothing) or may be contained in one or two or more modules which are detachable from the garment 102 prior to washing/drying the garment 102.

Controller 106 may also include processing electronics for performing some or all required signal processing on the sensed signals acquired from electrodes in sensors 104A-104C. In one or more embodiments, such signal processing (e.g., amplifying or filtering) may be performed locally in one or more of the sensors 104A-104C, at the controller 106, or both, for example. Controller 106 may also include signal processing for performing data analysis and feedback data generation. In one or more embodiments, such data analysis and feedback data generation may be performed at one or more of controller 106, SPCD 112, feedback device 114 (if such feedback device is other than SPCD 112 and/or effector 110, and/or the Internet 120. Signal processing for performing data analysis and feedback data generation may occur solely in the garment 102 and its associated electronic circuitry, external to garment 102, or both where some portion of the processing is done in the garment and other portions are done external to the garment 102 using processors and resources of external devices and/or systems.

Controller 106 may include one or more processors, multi-core processors, one or more digital signal processors (DSP), one or more micro-processors, one or more microcontrollers, one or more application specific integrated circuits (ASIC), one or more field programmable gate arrays (FPGA), one or more analog-to-digital converters (ADC), one or more digital-to-analog converters (DAC), a system on chip (SoC), one or more operational amplifiers, custom logic, programmable logic, analog circuitry, mixed analog and digital circuitry, or the like, just to name a few. Garment 102 may include one or more radios configured to transmit, receive, or both, radio frequency (RF) signals for one or more wireless communications links. A plurality of radios may communicate using a plurality of wireless protocols and the plurality of wireless protocols may be different protocols.

Alternatively, raw or partially (incompletely) processed sensor data can be transmitted off board to a cellphone or other SPCD device where data manipulation is accomplished. Resulting derived data can be transmitted back to the controller to initiate feedback to the wearer and/or adjust the functionality of the garment. This shifts the weight, power consumption and expense of computational components off board of the garment.

To provide power to the processing electronics and/or communication electronics and/or sensors, a power source such as one or more batteries (which may be rechargeable by various means or may be one-time-use, disposable batteries) may be incorporated into the form-fitting sensor garment in a permanent or detachable manner. If the electronics and/or power source are/is non-detachable, it is preferable that these components are constructed such that they can withstand repeated washing and drying cycles typical of wearable clothing. Alternative power sources may be used, as is discussed elsewhere herein.

For example, electrical power may be provided by a battery pack 118, which may be attached to form-fitting sensor garment 102 in a permanent or detachable manner. Battery pack 118 may represent a one-time-use, disposable battery or may represent a rechargeable battery pack (e.g., Lithium-Ion, Nickel Metal Hydride, or the like) to be recharged for use via a charging port (e.g., a micro USB connector) provided with a water resistant cap or plug implemented with battery pack 118 or on form-fitting sensor garment 102 or via a wireless charging technology such as inductive charging. The battery pack 118 (rechargeable or otherwise) may be configured to be replaceable (e.g., by the user) in the event the battery fails or to swap out a battery with low charge or no charge, with a freshly charged battery, for example. Battery pack 118 may be configured to accept batteries with different amp-hour capacities to provide sufficient duration of operation of garment 102 and its associated electronics, such as 1500 mAh, 3000 mAh, etc. Battery pack 118 may be configured to endure several wash cycles, dry cycles or both. Alternatively, battery pack 118 may be configured to be removable from garment 102 when the garment 102 is to be washed and/or dried.

Power may alternatively be obtained by on board generators, such as rotational generators positioned at the hip or knee to take advantage of reciprocating joint rotation. Other energy scavenging sources can take advantage of body temperature, respiration, stride (e.g., foot strike) or others as is understood in the art.

Vibrators or other effectors can be carried by the garment to be positioned at specific locations on the body which correlates with the nature of the desired proprioceptive feedback. Thus the wearer can receive a perceptible feedback which provides different instructions to the wearer depending upon the location of the effector. Activation may be pulsed or continuous until sensors determine that the desired correction has been accomplished. The frequency of pulsed feedback and/or the intensity of the feedback (e.g., vibration) can increase in proportion with the degree to which a target value is exceeded. A stepped feedback protocol can also be programmed, such that a first effector is activated when a first value is reached, and a second effector is activated when a second value is reached, typically at a greater deviation from the desired target than the first value. The value can be any measured parameter of any of the sensors disclosed herein.

An effector may be positioned, for example, on any or all of the posterior side of one or both lower or upper legs, activation of which tells the wearer to make a modification such as increase stride length or tempo. Certain effectors such as a tempo effector, pulse alarm limit, temperature alarm limit or anaerobic threshold alarm effectors do not need locational specificity so can be mounted any convenient location such as back or chest or side if that location is not needed to receive feedback that in combination with location conveys additional information to the wearer.

In general, sensors and/or effectors can be placed at any one or combination of the anterior right or left side or the posterior right or left side of the lower leg, upper leg, waist, glut, lower arm or upper arm. On the core or torso, effectors can be located on anterior, posterior or lateral sides, at the cervical, thoracic lumbar or sacral level of the spine, as well as the head, left or right hand or left or right foot. The wearer can be taught to move the portion of the body in the vicinity of a given effector towards or away from the direction of the effector in response to activation, or to accomplish some other behavioral modification in response to each effector activation.

Any of the effectors can be activated in response to data acquired by onboard sensors, or sensors carried by any of a variety of commercial activity trackers, smart watches, smart phones, etc., including those produced by Fitbit, Jawbone, Under Armour, Basis, Runtastic, Garmin among others, which can pair to the garment of the present invention via protocols such as Bluetooth, ANT+ or others known in the art.

One preferred effector comprises a device which when activated produces tactile sensation such as from a pressure or vibration against the skin. Small effective vibrators can comprise a small motor having a rotatable shaft, with a weight eccentrically carried by the shaft. The weight throws the shaft out of balance and produces vibration of the entire assembly. The vibrators may be permanently mounted on the garment, or may be detachable such as for washing, repositioning or replacement. The vibrator and any associated wiring is preferably water proof and can sustain wash and dry cycles. One suitable overmolded, waterproof vibrator is disclosed in US patent publication No. 2014/0265677 to Orand, the disclosure of which is hereby incorporated by reference in its entirety herein.

One effector that can change the resistance to movement across a joint such as a hip or knee is an adjustable rotary damper that can provide more or less resistance to rotation by variation in viscosity in response to an applied electrical signal. One type of adjustable rotary damper is filled with a magnetorheological fluid (MRF) which is a suspension of magnetically polarisable particles in a carrier fluid, the viscosity and other rheological properties of which can be changed rapidly and reversibly in a magnetic field. Analogously thereto, electrorheological fluids (ERF) are suspensions of electrically polarisable particles in a non-conductive carrier fluid, the rheological properties of which can be changed rapidly and reversibly in a magnetic field. Both classes of fluids hence offer an ideal basis for adaptive damping devices, the resistance to rotation of which are controlled by the magnetic field or the electrical field, in response to a signal from the controller 14.

The magnetizable particles are metal or metal oxide particles with size on the order of a few microns. The carrier liquid may also be referred to as a non-magnetic liquid, such as base oil. Additionally, surfactants may be used to allow for high particle volume fractions to increase the fluid's stability. Normally, the magnetic particles are randomly distributed in the liquid while no magnetic field is applied, and the suspensions behave as regular liquid. If the suspensions are exposed to a magnetic field, its flow resistance increases. This is because the magnetic particles form chain-like structures parallel to the magnetic field as a result of the magnetic interaction. The rheological properties as shear modulus and viscosity reversibly can change in milliseconds. The chain-like structure can be deformed and destroyed due to external forces, but they will quickly re-form as the external force is decreased or removed.

Controlled by the electromagnet, even small amounts of MR fluid can generate a large and smooth resistive force when the magnetic field is strong. Thus, the unit can be quite small and compact, which allows the exercise garment to be light-weight and portable.

At least one or two or more on board sensors can be used to detect the signals of the user's performance such as speed, torque, force, training time etc and/or the signals of the user's physical conditions such as oxygen level, breathing rate and heart rate. The sensors, MR unit and microprocessor in controller 14 can form a closed-loop system.

The device may be programmed so that the resistive force of the MR unit is adjusted in response to the level of a sensed value or a degree of deviation of the sensed value from a predetermined target value. The device may also allow for the user to modify various settings, such as the level of difficulty, purpose of exercise (e.g. strength training, rehabilitation, etc.), and other variables that will allow the user to customize the manner in which the MR damper responds to their physical activity. The controller 14 can take the customized setting as target and use a control algorithm to adjust the resistance of MR liquid. The controller 14 may be programmed to read the sensor values, then compute the desired output by calculating proportional, integral, and derivative responses and summing those three components to compute the output. In this closed loop system, the resistive force is the system parameter to be controlled. The sensor reading provides the feedback to the control system. The wearer's customized setting is the desired set point. At any given moment, the difference between the sensor readout and the set point is used by the control system algorithm (compensator) to determine the desired output to drive the system. For instance, if the sensor readout is lower than the set point, then the output specified by the control algorithm might be to increase the resistance. Additional details of MR damper systems can be seen in US patent publication No. 2013/0260968 to Shkolnik, the disclosure of which is hereby incorporated by reference in its entirety herein.

Referring to FIG. 3, at a stage 202, optionally a reference data set may be obtained. The reference data set may represent the reference data associated with a given activity, exercise, recorded prior history or programmed performance objective. For example, a bicep curl exercise may be represented by a data set that specifies the level of exertion that should be experienced by the bicep muscle (e.g., fairly high) and lower back muscle (e.g., fairly low). The data set may include one or more other aspects including but not limited to one or a combination of workout and/or exercise parameters, user specific parameters (e.g., BMI, percent body fat, weight, etc.), or electrode environmental parameters (e.g., sweat, body hair, etc.).

Reference data may also be generated by the wearer's previously stored data. Previous data can be maintained as a commencement to date cumulative data such as average, cumulative total, peak, high or low intensity, etc., or specific sessions may be elected to form the reference. For example a wearer might run a short distance (e.g., a quarter mile) maintaining what they consider an ideal form in terms of overall speed, stride length, stride tempo, arm swing, respiration or other measurable parameter, the data for which is saved as the reference. Then while running a longer distance such as a marathon, feedback is transmitted to the wearer via the corresponding effector as their body motion deviates from the stored reference so that conscious effort can be exerted to restore the motion parameter back to the reference. This may allow the runner to decouple fatigue from decreases in efficiency, to the extent that the inefficiency is now brought to the attention of the runner and potentially corrected to the extent permitted at a given level of fatigue.

At a stage 206, data may be acquired by sensors 104A-104C (or other sensors) while the user performs the exercise and transmitted to logic for analysis. The data may be communicated via signal conductors 108 (as mentioned in connection with FIG. 2) to controller 106. Analysis may be performed at controller 106 if controller 106 is endowed with logic and/or algorithms (e.g., software and/or hardware and/or firmware) to perform the analysis (in which case controller 106 may have to access to the earlier discussed reference data at the stage 202 for analysis purpose). This is shown by a path for signal conductors 108 in FIG. 2. Although all of the sensors 104A-104C are depicted directly coupled to a single controller 106, it should be understood that such coupling may be an actual/physical coupling or may be a logical coupling. For example, multiple controllers (e.g., multiple controllers 106) may cooperate to share the data processing task or to relay information from one or more sensors to the appropriate controller or controllers for further data processing.

Alternatively, the data may be communicated from sensors 104A-104C to controller 106 and then may be relayed to SPCD 112 for analysis (in which case SPCD 112 may have access to the earlier discussed reference data at the stage 202 for analysis purpose). Typically, wireless communication among components of textile-based human MAF system 100 may employ any suitable air interface, including for example Bluetooth™ (in its various implementations, including low power Bluetooth), ANT™, WiFi™, WiMAX™, infrared, cellular technology (such as for example GSM™, CDMA™, 2G™, 3G™, 4G™, 5G™, LTE™, GPRS™), etc. The selection of the appropriate air interface for communication depends on the air interface availability in the devices and/or at the location, cost, convenience, and/or other factors.

Alternatively or additionally, the data may be forwarded from SPCD 112 to Internet 120 (e.g., via path 164/156 or path 108/154/156) or from controller 106 to Internet 120 bypassing SPCD 120 (e.g., path 108/158) for analysis by one or more remotely implemented computers (e.g., 198, 199) through Internet 120.

Alternatively, the data may be communicated from sensors 104A-104C directly to Internet 120 for analysis (in which case the sensors 104A-104C may be equipped with communication circuitry such as wireless communication circuitry, and computers (e.g., 198, 199) implemented via the Internet 120 may have access to the earlier discussed system schema at the stage 202 for analysis purpose). Computers (e.g., 198, 199) may be in wired or wireless communication (198a, 198b) with the Internet 120.

Analysis at a stage 208 may include, in one or more embodiments, comparing the exertion level of individual muscles (e.g., obtained from the muscle activation data from the sensors 104A-104C) with the reference exertion level of those muscles (e.g., obtained from the reference data at the stage 202). This analysis may reveal, for example, whether the human subject is performing the exercise at the appropriate intensity level (e.g., by looking at the intensity data from the sensors 104A-104C and comparing such information with corresponding information in the reference data at the stage 202). This analysis may also reveal, for example, whether the human subject is performing the exercise or activity incorrectly. This may be the case if, for example, one muscle in the group of muscles under monitoring by the sensors 104A-104C is over-exerted or under-exerted. Other sensor data such as bend-angle sensor data or accelerometer sensor data may be used to compare parameters such as acceleration, velocity, other motion or position to the reference data.

Analysis at the stage 208 may include, alternatively or additionally, comparing the duration of the exertion of individual muscles (e.g., obtained from the muscle activation data from the sensors 104A-104C) with the reference exertion duration of those muscles (e.g., obtained from the reference data at the stage 202). Analysis may include, alternatively or additionally, comparing the number of exertion repetitions in a set (obtained from the muscle activation data from the sensors 104A-104C) with the reference exertion repetitions for those muscles (e.g., obtained from the system schema at the stage 202), repetition rate, angular range of motion, etc.

Analysis at the stage 208 may include, alternatively or additionally accumulating an activity score based on an electromyography signal. Such a score may be in different resolution forms such as the overall body or individual muscles. This allows the user to compare intensity level as measured through muscle exertion over time.

Analysis at the stage 208 may include, alternatively or additionally determining the number of repetitions and an approximation of the weight used. Such analysis may be determined by statistical analysis on saved user data or by comparing the user data against a larger data set of all active users stored in Internet 120 in FIG. 2. User data may be stored on one of controller 106, SPCD 112 or equipment 110.

Analysis at the stage 208 may include, alternatively or additionally updating a user profile and comparing against profiles of one or more other users. In one embodiment, user profile data may include a history of workout sessions including overall exertion as well as individually monitored muscles. In another embodiment, profile data may include goals set by the user and additionally or alternatively challenges from other users (e.g., to motivate the user). For example, the challenges may come from other persons or users who may be associated with a social network (e.g., Facebook®, Twitter®), professional network (e.g., LinkedIn®), or the like. Through social and/or professional networking of user profiles including historical workout data, motivation is increased by the competitive environment created. Additionally, challenges may be proposed by the system (e.g., controller 106 and/or other system in communication with controller 106). A combination of progressive challenges (e.g., a series of challenges, each with higher goals to be achieved) may lead the user to higher and higher levels as in a gaming scenario were gameificaiton of the challenges may comprise the user taking on progressive challenges against goals set by the user, the system, others, or by other competitors in the game, for example.

A result of the analysis at the stage 208 may be immediately communicated to the user at a stage 210 via a display 112a of device 112 (e.g., a smartphone, table, pad, eyeglasses 182, etc.) or an auxiliary feedback device such as devices 114 including any of the effectors disclosed elsewhere herein substantially in real time (e.g., immediately after data acquisition and analysis is completed, factoring in real-world delays in data transmission and processing).

Feedback at the stage 210 may, for example, include a representation of the body and visually depict the muscles being exerted, along with a color gradient or an overlay with relative exertion or other data depiction scheme to communicate the intensity level and/or duration and/or number of repetitions associated with each muscle. The feedback at the stage 210 may also include recommendations in the form of audio, visual (e.g., lights, text) or proprioceptive (e.g., push more with the left arm; increase or decrease stride length; increase or decrease stride rate; adjust body position) or status or warning (e.g., move elbows medially; crossing anaerobic threshold; body temperature exceeding or falling below a preset alarm limit; pulse exceeding a preset alarm limit; hydration status falling below a preset alarm limit; etc.) or other coaching information while the human subject is performing the exercise.

Additionally, feedback at the stage 210 may be stored on either the controller 106, the SPCD 112 or the Internet 120 for later viewing and/or audio playback. In one example, after completing a set or portion of a workout session the user may "playback" visual features including the body representation with muscle depiction. This allows the user to get feedback at a time that is convenient and not during a strenuous activity. Other features can be added to compare the "playback" with other users who may be a part of the system environment. For example using a professional athlete as a benchmark of comparison.

Feedback device 114 may be implemented by a built-in display 112a of SPCD 112 (e.g., a LCD, OLED, touch screen, etc.) by an external display 170, by audio playback device (such as headset 180, which may be in communication with controller 106, SPCD 112, external display 170 and/or Internet 120), or by digital eyewear (see 182 in FIG. 1A). Feedback device 114 may provide feedback information in either graphical, video, or audio format to the user.

For example, the analysis result at the stage 208 (e.g., as a type of feedback at the stage 210) may be displayed on the display screen 112a of SPCD 112 after analysis by SPCD 112. Alternatively, the analysis result may be displayed (e.g., using wireless communication if necessary) on the display screen 112a of SPCD 112 if analysis takes place elsewhere (e.g., communicated via path 154 if analysis is performed on controller 106 or via path 156 if analysis is performed via Internet 120). Alternatively or additionally, the analysis result may be displayed on an external display 170 (e.g., communicated via path 172 or path 154/174 if analysis is performed on controller 106 or communicated via path 156/174 or path 176 if analysis is performed by Internet 120).

Alternatively or additionally, the analysis result at the stage 208 may be displayed on digital eyeglasses (see 182 in FIG. 2) instead of external display 170. Alternatively or additionally, the analysis result at the stage 208 may be converted to an audio format and played back using a headset 180 (e.g., a wireless headset, earpiece, headphones, or the like, or conveyed via one or more proprioceptive effectors which may be located in a predetermined position on the garment so that the wearer can correlate that position with the nature of the information conveyed at that position).

The analysis result at the stage 208 may be employed to alter the behavior of the exercise garment in order to improve the exercise experience and/or exercise form or efficacy for the wearer. For example, if the user is perceived to employ bad form while exercising at a given intensity level, the resistance level across the hip joint, knee, elbow, shoulder or other motion segment may be automatically reduced (e.g., in real time, using an effector operating under the command of controller 106 or SPCD 112) in order to help improve the form of the wearer. Contrarily, if the analysis at the stage 208 reveals that the user can rapidly perform the exercise without much muscle strain, the resistance level may be elevated (e.g., in real time) in order to present a more meaningful or beneficial exercise to the human subject.

In accordance with one or more embodiments, form-fitting sensor garment 102 (or more specifically controller 106 of form-fitting sensor garment 102) may automatically pair with SPCD 112. Pairing, in the context of the present invention, may pertain to the association of a specific device with another specific device to facilitate wireless data communication and/or wireless data security/confidentiality. Likewise, form-fitting sensor garment 102 (or more specifically controller 106 of form-fitting sensor garment 102) may automatically pair (e.g., BT paring) with exercise equipment 190 (or more specifically with exercise equipment communication device 110 thereof). Likewise, SPCD 112 may automatically pair with exercise equipment 190 (or more specifically with exercise equipment communication device 110).

In one or more embodiments, form-fitting sensor garment 102 (or more specifically controller 106 of form-fitting sensor garment 102) may intelligently pair with SPCD 112 to reduce power consumption (e.g., from battery pack 118). In an example of intelligent pairing, the communication apparatus would be turned off during periods of inactivity, such as when the user is resting. When controller 106, through algorithmic implementation, detects the commencing of activity the communicating apparatus would be turned on and pairing completed. Likewise, form-fitting sensor garment 102 (or more specifically controller 106 of form-fitting sensor garment 102) may intelligently pair with exercise equipment 190 (or more specifically with exercise equipment communication device 110 thereof) to reduce power consumption. Likewise, SPCD 112 may intelligently pair with exercise equipment 190 (or more specifically with exercise equipment communication device 110) to extend battery life. In other embodiments, processor 106 may scan for sensor activity from one or more of the sensors (e.g., 104A-104C) and if no sensor activity is detected, then processor 106 may switch to a low power mode of operation (e.g., to conserve battery power). Upon detecting sensor activity, processor 106 may exit the low power mode, analyze the detected sensor activity (e.g., analyze signals from the sensors) and take appropriate action. In some examples, the appropriate action may comprise the processor 106 switching back to the low power mode of operation, because the signals analyzed were not indicative of the type of activity the sensor is intended to sense, for example. Lack of motion or other physical activity or lack thereof by user may serve to trigger entry into the low power mode of operation for processor 106. For example, sensor not detecting muscle activity may prompt processor 106 to switch to the low power mode of operation. Subsequently, detection of muscle activity may prompt processor 106 to exit the low power mode of operation. As another example, a motion sensor (e.g., an accelerometer, motion detector, or gyroscope) may output a signal indicative of no motion or motion below a threshold indicative of sufficient activity by user and that signal may prompt processor 106 to switch to the low power mode of operation. Subsequently, motion detector may generate a signal indicative of sufficient activity by user (e.g., running, walking, etc.) and processor 106 may switch out of the low power mode of operation to another mode where the signal from motion detector is analyzed and acted on.

Likewise, form-fitting sensor garment 102 (or more specifically controller 106 of form-fitting sensor garment 102) may automatically pair with the external display 170 or the headset 180 or the digital eyeglass 182 as described earlier. Likewise, SPCD 112 may automatically pair or otherwise establish a wireless communication link (e.g., via BT, WiFi, 2G, 3G, 4G, 5G, or other protocol) with one or more of the external display 170, the headset 180, or the digital eyeglass 182 as described above.

Figure 7:
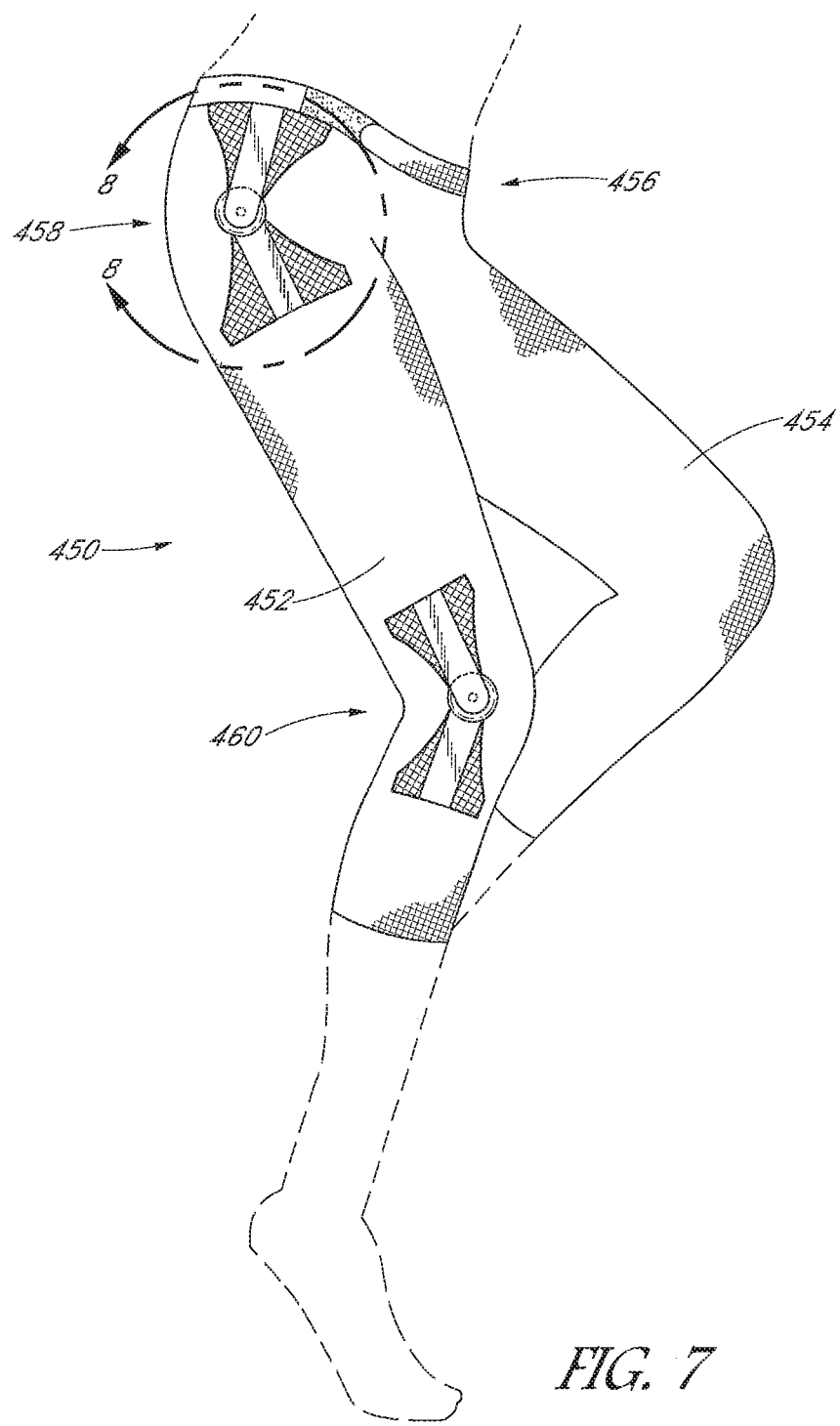
FIG. 7 is a side elevational view of a garment, having resistance and dynamic proprioception devices mounted thereon.

Referring to FIG. 7, there is illustrated a further toning garment 450 in accordance with the present invention. The toning garment 450 includes a right leg 452, a left leg 454, and a waist 456. As for all garments disclosed herein, the toning garment 450 will preferably be bilaterally symmetrical. Accordingly, only a single side will be discussed in detail herein.

In the illustrated embodiment, the right leg 452 is provided with a hip resistance unit 458. Right leg 452 is additionally provided with a knee resistance unit 460. Each leg of the toning garment 450 may be provided with either the hip resistance unit 458 or the knee resistance unit 460, with or without the other. The left and right hip resistance units will preferably have an axis of rotation that is functionally aligned with a transverse axis of rotation which extends through the wearer's left and right hip axes of rotation. Functional alignment includes precise alignment however due to the different fit that will be achieved from wearer to wearer, precise alignment may not always occur. Due to the stretchability of the garment, minor misalignment may self correct or not present adverse performance. Similarly, the knee resistance units, if present, will preferably have an axis of rotation that is functionally aligned with the transverse axis of rotation that extends through the center of rotation of each knee. Compensation for misalignment is discussed below.

Figure 8:
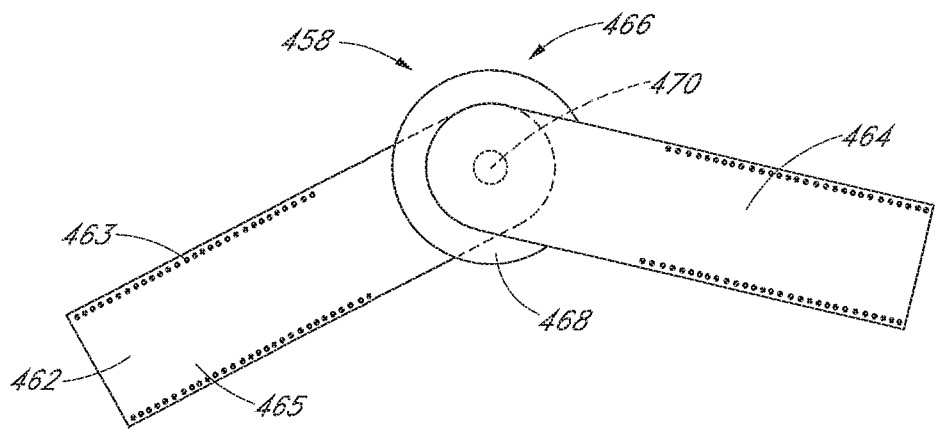
FIG. 8 is a detail view of one of the resistance and dynamic proprioception devices of FIG. 7.

Referring to FIG. 8, the hip resistance unit 458 will be described in further detail. The left leg hip resistance unit, and both the right and left leg knee resistance unit 460 may be constructed in a similar manner. The unit has an outer housing, which may enclose a rotary damper. Housing may also enclose processing electronics described elsewhere herein, as well as a power supply and transmitter or transceiver for communicating with other components in the system.

The hip resistance unit 458 is provided with a first attachment such as a first lever 462, and a second attachment such as a second lever 464 connected by a pivotable connection 466. The pivotable connection 466 comprises a resistance element 468 which provides resistance to angular movement between a primary longitudinal axis of first lever 462 and a primary longitudinal axis of second lever 464. In the as worn orientation, the axis of rotation 470 is preferably substantially aligned with an axis of rotation of the joint with which the resistance element is associated.

A lever as used herein refers to a structure that mechanically links a housing or rotatable component of a resistance unit to a portion of the garment or wearer at or above or below the resistance unit, so that movement of the wearer is resisted by the resistance unit without undesirable stretching of the garment. The lever may take a conventional form, as illustrated in FIG. 8, and comprise an elongate element having a length generally at least about 2 inches, in some embodiments at least about 4 or 6 or 8 inches to provide better leverage and attachment force distribution. The element may a have a width of at least about 0.25 inches, and in some embodiments at least about 0.5 inches or 1.0 inches or 2 inches or more but normally less than about 3 inches or 2.5 inches. The thickness may be less than about 0.25 inches, preferably less than about 0.125 inches and in some embodiments less than about 0.050 inches. The lever may comprise any of a variety of washable, non-corrosive materials such as nylon, Teflon, polyethylene, PEBAX, PEEK or others known in the art. Preferably the lever arm is sufficient to transmit force in the anterior-posterior direction in the case of hip and knee resistance units, but is flexible in the medial-lateral direction to enable the garment to follow the contours of the body.

The inferior and superior lever arms may be similar to each other for a resistance unit mounted at the knee. For a resistance unit mounted at the hip, the lever arms may be distinct. For example, the inferior lever arm at the hip may conveniently comprise an elongated femoral lever, such as that illustrated in FIG. 7, in which the axial length of the lever is at least about two times, and may be at least about five times or eight times its width. This lever arm can extend down the lateral side of the leg, secured by the garment approximately parallel to the femur.

The superior lever arm may have a vertical component towards the waist, with a bend so that a superior component extends in a transverse direction, either partially or completely circumferentially around the waist of the wearer. Alternatively, the superior lever arm may comprise a fabric or plastic force transfer patch, such as a circular, square, rectangular, oval or other shape which can be secured to the rotational damper or a docking station for receiving the rotational damper, and also secured to the garment in a manner that resists rotation of the damper with respect to the garment during movement of the inferior lever. Thus, "lever" as used herein is a force transfer structure and is not limited to the species of a conventional elongate arm.

The lever may alternatively comprise a hub for attachment to the resistance unit, and a plurality of two or three or four or more elements that are secured such as by stitching or adhesive bonding to the garment. Each of the elements is preferably relatively inflexible in the anterior-posterior direction, but flexible in the medial-lateral direction to enable an anterior element to wrap at least partially around the side and optionally around the front of the leg. A posterior element preferably wraps at least partially around the posterior side of the leg. The elements can comprise one or more strands or technical fabric supports, sufficient to transmit the forces involved in a given garment and resistance unit system.

The hip resistance unit 458 may be secured to the toning garment 450 in any of a variety of ways. The first lever 462 may be provided with at least a first set of apertures 463 and optionally a second set of apertures 465 to receive a filament such as a polymeric or fabric thread, for sewing the hip resistance unit 458 to the garment. Stitching may alternatively be accomplished by piercing the first lever 462 directly with the sewing needle, without the need for apertures 463 or 465. Alternatively, the first lever 462 can be secured to the garment using any of a variety of fastening techniques, such as adhesive bonding, grommets or others known in the art.

A lever is convenient for the inferior attachment, to distribute force along a portion of the length of the femur. The longitudinal axis of the first, superior attachment at the hip may be transverse to the longitudinal axis of the second lever 464 at the midpoint of its range of motion, such that the first lever is aligned like a belt, circumferentially extending along a portion of or approximately parallel to the wearer's waist. Normally the hip axis of rotation will be offset inferiorly by at least about 3 inches, and often 5 inches or more from the iliac crest, which approximates the belt line for many wearers. Alternatively, the housing of the resistance element may be sewn or adhesively bonded or otherwise attached directly to reinforced fabric at the hip.

The rotary damper may be rated to provide anywhere within the range of from about 0.1 inch pounds to about 50 inch pounds torque depending upon the joint or other motion segment to be loaded and desired intensity. Generally, in a toning garment, torque at the hip may be in the range of from about 2 inch pounds to about 8 inch pounds, and often no more than about 6 inch pounds. For the athletic training market, higher torques such as at least about 3 or 5 or 7 inch pounds, and some implementations at least about 10 or 15 inch pounds or higher may be desirable at the hip. In some implementations, the resistance element provides at least about 6 or 8 or 10 or 12 inch pounds and possibly 15 inch pounds or more depending upon garment construction, measured at 40 degrees per second.

Torque at the knee will generally be less than at the hip. Values of generally no more than about 85% or 50% or 35% of the torque at the hip may be desirable in a toning garment at the knee, measured at 30 RPM for fully rotational dampers at approximately STP. As discussed elsewhere herein, the resistance element at any given joint can provide the same or different resistance (including zero) upon flexion or extension.

Figure 9:
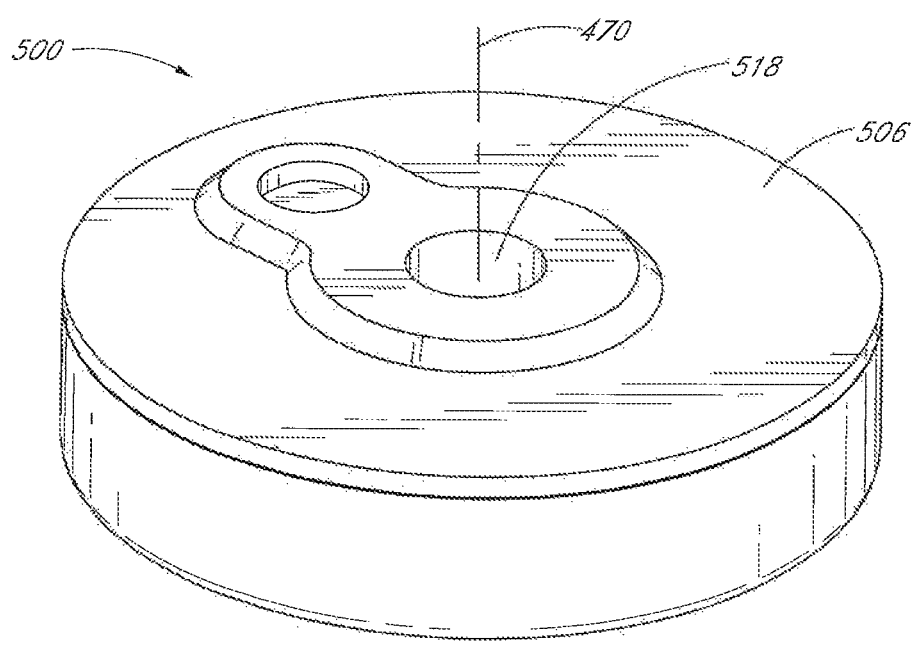
FIG. 9 is in enlarged perspective view of a rotary damper resistance unit useful in the present invention.
Figure 10:
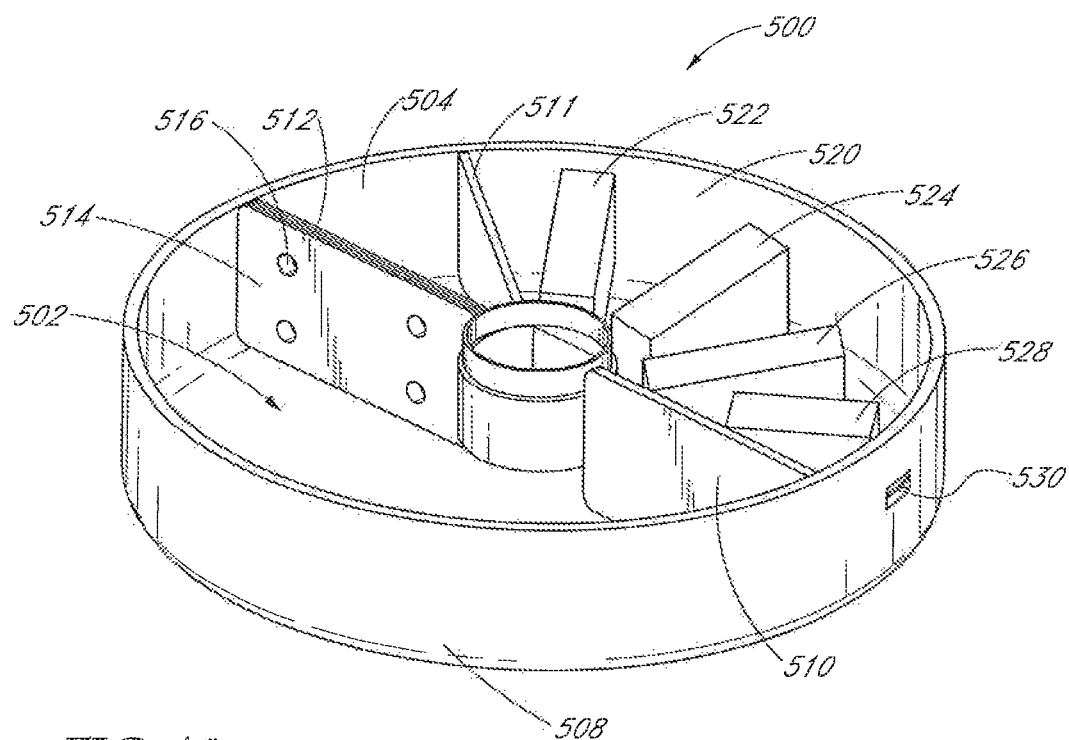
FIG. 10 is a perspective view of the rotary damper of FIG. 9, with a portion of the housing removed to reveal a rotational resistance subassembly and an electronically enabled subassembly.

Referring now to FIGS. 9-10, a rotary damper resistance element is illustrated. Any of a variety of alternative specific damper constructions may be utilized as will be apparent to those of skill in the art. Linear dampers may also be used, along with associated lever arms, or mounted in line in a pulley system. The apparatus includes a housing 500 defining a housing interior 502 for containing damper fluid (not shown) of any conventional nature, and optimally also electronic components. The housing interior has a substantially circular cross section and is formed by a toroidal or cylindrical (illustrated) inner housing surface 504 disposed about and spaced from a central axis 470. The housing 500 includes two adjoining housing members 506, 508, each housing member defining a portion of the housing interior.

A vane or piston 514 having an outer peripheral piston surface at which is located an outer seal 512 is in substantially fluid-tight, slidable engagement with the inner housing surface, spaced from axis 470 and disposed along a common plane with the axis 470. The housing 500 and the piston 514 are relatively rotatably moveable about the axis, as will be described in greater detail below.

A first fluid barrier 510 and a second fluid barrier 511 each in the form of a plate are immovably attached to the housing and positioned in the housing interior.

The vane 514 defines multiple flow control orifices or passageways 516 which permit restricted passage of damper fluid therethrough responsive to relative rotational movement of the vane 514 throughout an angular range between the first fixed barrier 510 and second fixed barrier 511 to dampen forces applied to the apparatus causing the relative rotational movement.

A shaft or aperture 518 extends through the housing interior along axis 470 and is exposed on at least one opposed side of the housing, for connection as has been discussed.

Piston 514 is secured with respect to shaft or a sidewall of aperture 518 such that relative rotational movement between the housing and the aperture 518 causes the piston 514 to rotate through an arc about axis 470. This will cause damper fluid in the housing interior to pass through flow control passageways 516 and thus resist the relative rotational movement.

In the illustrated embodiment, the barriers 510 and 511 define a first portion 504 of the housing interior 502 for containing viscous fluid, and enabling piston 514 to rotate throughout an angular range of motion. The hip normally rotates in the anterior posterior plane throughout a range which varies from individual to individual and based upon speed of travel, but is generally from about 35° for short walking strides to a maximum of no more than about 120° for most wearers. The knee, elbow and other motion segments also have a limited range of motion. Thus a full 360° range of motion at the resistance unit is not necessary. The barriers 510 and 511 thus also define an electronics component chamber 520 which is isolated from the damper chamber 504. Electronics component chamber 520 may include any of a variety of electronic components, depending upon the functionality of the device. For example, a power supply 522 such as a battery may be provided. Also illustrated is a central processing unit 524, a transmitter or transceiver 528 and potentially one or more sensors 526.

Figure 11:
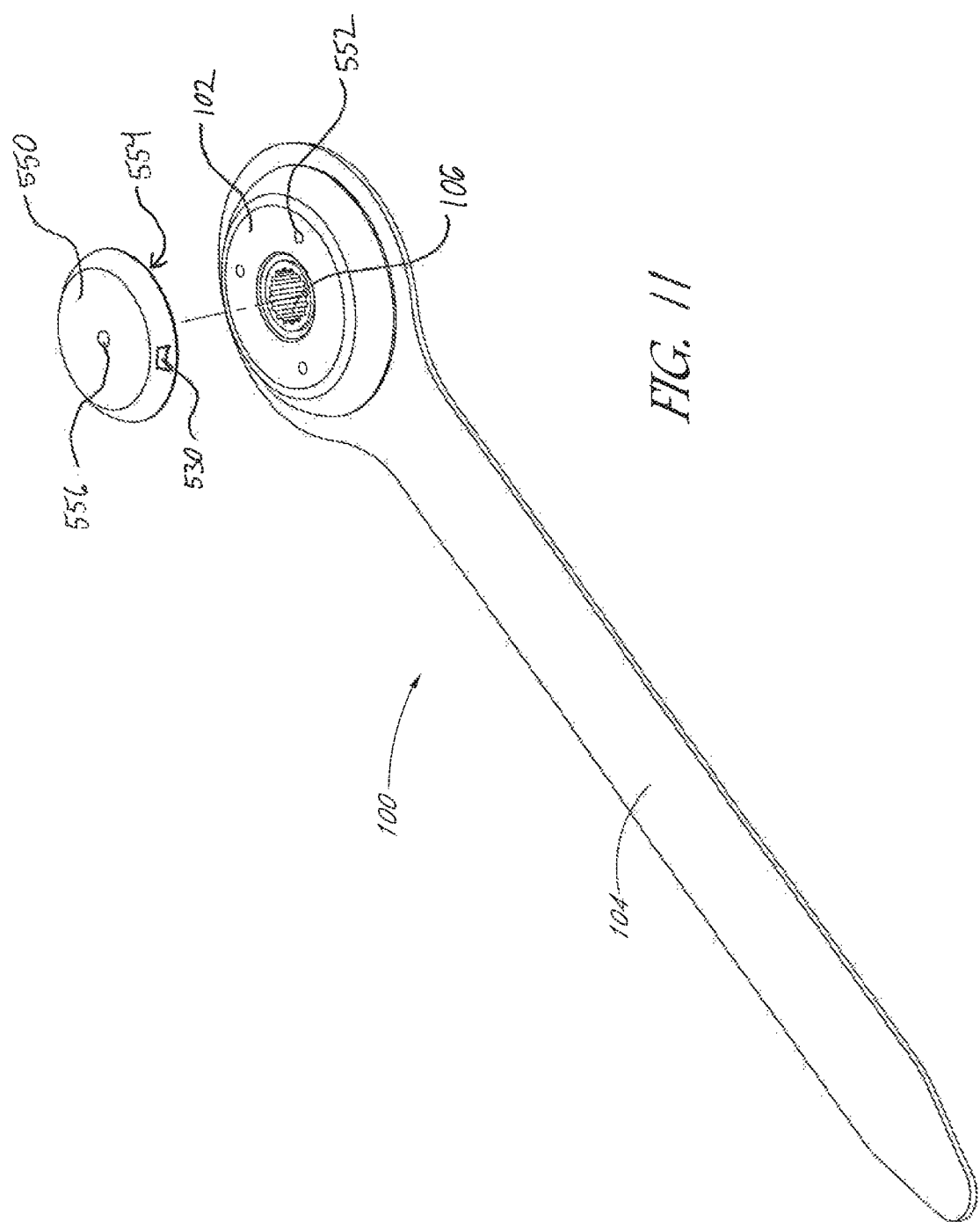
FIG. 11 is an exploded view of a resistance unit and an interchangeable electronic module.

The electronics component chamber 520 may alternatively or additionally be carried in a separate removable, interchangeable electronically enabled module 550 as illustrated in FIG. 11. The electronics module comprises a housing having at least one chamber therein for containing any one or more of the electronic components or systems disclosed elsewhere herein. The housing has a lower docking surface 554 having at least a first connector (not illustrated) configured to releasably connect to a second, complementary connector 552 on a resistance unit 100 or resistance element 102. Any of a variety of mechanical interference fit structures may be used for snap fit, threaded fit or other releasable engagement. One or two or three or four or more complementary pairs of connectors may be utilized. Magnetic attachment may also be used, with magnets carried by the resistance element positioned to align with complementary magnets of opposite polarity in the electronics module 550. ElectroPermanent Magnets or EPM's may be desirable, since the external magnetic field can be turned on and off by applying a current pulse, but no current is required to maintain the magnetic field once the EPM has been activated.

The electronics module 550 is also provided with a rotatable shaft or other rotation sensing or transferring element 556, to couple to the rotatable aperture or shaft of the resistance element. One or more electrical connections may also be provided on the docking surface 554, for placing the electronics module into electrical connection with the resistance element. For example a multiple pogo pin connector on one docking surface can be brought into alignment with a complementary multi conductor connector on the other complementary docking surface. Inductive communication may be desirable since it may have better durability in a damp environment. Electrical communication between the electronics module and the resistance unit may be desirable if some electronics such as certain sensors are preferably located within the resistance module or elsewhere on the garment.

An electronics module 550 may be multipurpose, and include electronics to enable any combination of functions described elsewhere herein. Alternatively, application specific modules may be produced to help reduce cost and tailor functionality to a particular wearer's needs. For example, a module may be configured to report any one or combination of incremental power, stride rate, stride length, or derived metrics such as power to heart rate ratio; power to weight ratio; efficiency factor or more depending upon the intended use. The electronics module may be configured solely as a data capture device, to be downloaded following the exercise period. It may alternatively be configured as both a data capture and transmit device, such as to transmit raw or processed data to a remote receiver, with or without any direct feedback to the wearer. The remote receiver may be a smart phone or other device capable of receiving and displaying the data, for use by a coach, medical personnel, or anyone who has a desire to see performance metrics. Multiple players or athletes on a team may simultaneously transmit performance data to the coach, who can monitor power output and other metrics of the team members side by side as they go through similar activities, for various evaluation purposes.

Power supply 522 may comprise a battery pack, which may be carried within the housing in a permanent or detachable manner. The battery pack may represent a one-time-use, disposable battery or may represent a rechargeable battery pack (e.g., Lithium-Ion, Nickel Metal Hydride, or the like) to be recharged for use via a charging port (e.g., a micro USB connector 530) provided with a water resistant cap or plug. Charging may alternatively be accomplished via a wireless charging technology such as inductive charging via an induction coil carried by or within the housing. The battery pack (rechargeable or otherwise) may be configured to be replaceable (e.g., by the user) in the event the battery fails or to swap out a battery with low charge or no charge, with a freshly charged battery, for example. Battery pack may be configured to accept batteries with different amp-hour capacities to provide sufficient duration of operation of the garment and its associated electronics, such as 1500 mAh, 3000 mAh, etc. Power supply 522 may alternatively comprise an on board generator, such as a rotational generator positioned at the hip or knee to take advantage of reciprocating joint rotation. Other energy scavenging sources can take advantage of body temperature, respiration, stride (e.g., foot strike) temperature change representing calories burned as a result of movement at the hip, which elevates the temperature of the damper, or others as is understood in the art.

Communication module 528 to permit electronics on the resistance unit and/or carried elsewhere on the garment to communicate (e.g., wireless data) with one or more of external, remote devices such as a smart personal communication device (e.g., a smart phone, tablet, or pad), remote feedback device, on board feedback device such as a vibrator, compression pad or ring, electrical current or other feedback effector, or any of a variety of tracker systems such as those produced by Fitbit, Jawbone, Nike's Fuelband or Under Armour's Healthbox connected ecosystem. Typically, wireless communication among components of the wearable fitness ecosystem may employ any suitable air interface, including for example Bluetooth™ (in its various implementations, including low power Bluetooth), ANT™, ANT+, WiFi™, WiMAX™, 802.11(x), infrared, cellular technology (such as for example GSM™, CDMA™, 2G™, 3G™, 4G™, 5G™, LTE™, GPRS™), etc. The selection of the appropriate air interface for communication depends on the air interface availability in the devices and/or at the location, cost, convenience, battery life and/or other factors.

The sensor module 526 can include any of a variety of sensors described elsewhere herein, depending upon the desired functionality. For example, temperature sensors may be provided both to enable correction of other sensor data or electronics due to thermal drift as the resistance unit rises in temperature, as well as to provide a metric of calories burned. Sensors for enabling the determination of force, power, stride length, stride velocity, stride rate among others may be conveniently placed on or within the resistance unit. For example, at least one or two or four or more accelerometers may be placed throughout the resistance unit, femoral lever or garment (e.g., left and right arm; left and right leg) and/or otherwise carried by the wearer's body (i.e., attached via any suitable manner to shoes, wrist bands, etc.) to collect multiple data points. Each of the additional accelerometers may be connected wirelessly or via electrical conductors back to the controller 524 and/or communication module 528. A suitable 3-axis accelerometer may be a model ADXL377 available from Analog Devices, Inc. of Norwood, Mass. or any equivalent. Likewise, a suitable 3-axis gyroscope may be a model ADXRS652 available from Analog Devices, Inc. of Norwood, Mass. or any equivalent. Raw data may be sent from both the 3-axis accelerometer and the 3-axis gyroscope to the controller 524 which can record acceleration, 3-axis gyroscope position in terms of x, y, and z coordinates. The controller 524 may obtain position point recordings multiple (e.g., 500 times) a second and is configured to automatically write the data points to memory along with transmitting the data over the communication interface to sensor data interpretation software which may be resident on a remote computing device (e.g., laptop, cell phone, etc.). Additional details of wearable gyroscope and accelerometer systems may be found in US patent publication 2014/03133049 to Doherty, the entirety of which is hereby incorporated by reference herein. Strain gauges, piezoelectric and proximity sensors may also be mounted on the resistance unit depending upon a variety of manufacturing choices and intended functionality.

The controller module 524 may also include processing electronics for performing some or all required signal processing on the sensed signals. In one or more embodiments, such signal processing (e.g., amplifying or filtering) may be performed locally in one or more of the sensors at the controller 524, or both, for example. Controller 524 may also include signal processing for performing data analysis and feedback data generation. In one or more embodiments, such data analysis and feedback data generation may be performed at one or more of controller 524, local remote device such as a fitness tracker or smart phone or the Internet. Signal processing for performing data analysis and feedback data generation may occur solely in the garment and its associated electronic circuitry, external to garment, or both where some portion of the processing is done in the garment and other portions are done external to the garment using processors and resources of external devices and/or systems.

Controller 524 may include one or more processors, multi-core processors, one or more digital signal processors (DSP), one or more micro-processors, one or more microcontrollers, one or more application specific integrated circuits (ASIC), one or more field programmable gate arrays (FPGA), one or more analog-to-digital converters (ADC), one or more digital-to-analog converters (DAC), a system on chip (SoC), one or more operational amplifiers, custom logic, programmable logic, analog circuitry, mixed analog and digital circuitry, or the like, just to name a few. Alternatively, raw or partially (incompletely) processed sensor data can be transmitted off board to a cellphone or other smart local remote device where data manipulation is accomplished. This shifts the weight, power consumption and expense of computational components off board of the garment.

Analysis performed either on board the controller 524 or off board may include, in one or more embodiments, comparing an exertion level with the reference exertion level as is discussed elsewhere herein. Other sensor data such as bend-angle sensor data or accelerometer sensor data may be used to compare parameters such as acceleration, velocity, other motion or position to the reference data.

Analysis may also include, alternatively or additionally updating a user profile and comparing against profiles of one or more other users. In one embodiment, user profile data may include a history of workout sessions including overall exertion as well as individually monitored muscles. In another embodiment, profile data may include goals set by the user and additionally or alternatively challenges from other users (e.g., to motivate the user). For example, the challenges may come from other persons or users who may be associated with a social network (e.g., Facebook®, Twitter®), professional network (e.g., LinkedIn®), training partner, training team, or the like. Through social and/or professional networking of user profiles including historical workout data, motivation is increased by the competitive environment created. Additionally, challenges or goals may be proposed by the system (e.g., controller 524 and/or other system in communication with controller 524). A combination of progressive challenges (e.g., a series of challenges, each with higher goals to be achieved) may lead the user to higher and higher levels as in a gaming scenario where gameificaiton of the challenges may comprise the user taking on progressive challenges against goals set by the user, the system, others, or by other competitors in the game, for example.

As will be apparent to those of skill in the art in view of the disclosure herein, certain sensors are preferably mounted elsewhere on the garment but other sensors may be or preferably are mounted at or near the axis of rotation on the damper or damper housing. These may include force sensors, angular displacement sensors, accelerometers, proximity sensors, (potentially depending upon the manner in which data is obtained for the calculation of power) and temperature sensors, such as to directly measure caloric burn accomplished by the resistance unit. An external electrical connector 530 such as a mini USB port may also be provided on the housing, for electrical connection to an external device such as to charge the battery 522, program the CPU, and or download data which has been obtained during an exercise period or other data collection period. The CPU module may contain memory, and or a separate memory module may be provided depending upon the intended length of the data collection period and or the complexity (i.e., data rate) of the data being recorded.

While the present application has been described in terms of several preferred embodiments and/or examples, there may be alterations, permutations, and equivalents, which fall within the scope of the present application. The present application should be understood to also encompass these alterations, permutations, and equivalents. It should also be noted that there are many alternative ways of implementing the systems, methods, computer readable media, and apparatuses of the present application. Although various examples are provided herein, it is intended that these examples be illustrative and not limiting with respect to the present application.

Although the foregoing examples have been described in some detail for purposes of clarity of understanding, the above-described concepts are not limited to the details provided. There are many alternative ways of implementing the above-described concepts for the present application. The disclosed embodiments and/or examples are illustrative and not restrictive.

What is claimed is:

1. A dynamic proprioception garment, comprising:
   a waist region, a right leg and a left leg;
   a resistance unit associated with at least one of the right and left leg;
   a sensor; and
   an effector, separate from the resistance unit, for providing proprioceptive feedback to a wearer of the garment.

2. The dynamic proprioception garment as in claim 1, comprising at least one effector on the left leg and at least one effector on the right leg.

3. The dynamic proprioception garment as in claim 2, comprising at least one effector on a posterior of the left leg and at least one effector on a posterior of the right leg.

4. The dynamic proprioception garment as in claim 3, comprising electronics configured to activate at least one effector in response to a characteristic of stride reaching a preset alarm limit.

5. The dynamic proprioception garment as in claim 4, wherein the characteristic comprises stride rate.

6. The dynamic proprioception garment as in claim 4, wherein the characteristic comprises stride length.

7. The dynamic proprioception garment as in claim 1, wherein the location of the effector is correlated with a parameter of interest.

8. The dynamic proprioception garment as in claim 7, wherein the location of the effector is correlated with information relating to blood oxygen saturation.

9. The dynamic proprioception garment as in claim 7, wherein the location of the effector is correlated with information relating to heart rate.

10. The dynamic proprioception garment as in claim 7, wherein the location of the effector is correlated with information relating to body temperature.

11. The dynamic proprioception garment as in claim 7, wherein the location of the effector is correlated with information relating to power exertion.

12. The dynamic proprioception garment as in claim 7, wherein the location of the effector is correlated with information relating to respiration rate.

13. The dynamic proprioception garment as in claim 1, wherein the effector is configured to change the resistance provided by the resistance unit, in response to data obtained by the sensor.

14. The dynamic proprioception garment as in claim 1, comprising a left resistance unit having a left housing and a right resistance unit having a right housing.

15. The dynamic proprioception garment as in claim 14, comprising a left sensor in the left housing and a right sensor in the right housing.

16. The dynamic proprioception garment as in claim 15, further comprising a transmitter, for transmitting data to a remote device.

17. The dynamic proprioception garment as in claim 14, comprising a left rotary damper in the left housing and a right rotary damper in the right housing.

18. The dynamic proprioception garment as in claim 17, wherein the left rotary damper imposes a resistance of at least about 10 inch pounds.

19. The dynamic proprioception garment as in claim 18, wherein the left rotary damper imposes a resistance of at least about 15 inch pounds.

20. The dynamic proprioception garment as in claim 18, further comprising a first attachment and a second attachment connected by a pivotable connection.

21. The dynamic proprioception garment as in claim 20, further comprising a left femoral lever and a right femoral lever.

22. The dynamic proprioception garment as in claim 21, wherein at least one femoral lever has a length of at least about two inches.

23. The dynamic proprioception garment as in claim 22, wherein at least one femoral lever has a length of at least about four inches.

24. The dynamic proprioception garment as in claim 14, wherein the sensor comprises a force sensor.

25. The dynamic proprioception garment as in claim 14, wherein the sensor comprises an accelerometer.

26. The dynamic proprioception garment as in claim 14, wherein the sensor comprises a bend angle sensor.

27. The dynamic proprioception garment as in claim 14, wherein the sensor comprises a spatial deviation sensor.

28. The dynamic proprioception garment as in claim 14, wherein the sensor comprises a gyroscope.

29. The dynamic proprioception garment as in claim 14, wherein the effector comprises a vibrator.

30. The dynamic proprioception garment as in claim 14, wherein the effector produces a sound.

31. The dynamic proprioception garment as in claim 14, wherein the effector produces a visual indicator.

32. The dynamic proprioception garment as in claim 14, further comprising a processor.

\* \* \* \* \*